(12) United States Patent
Robinson

(10) Patent No.: US 11,098,086 B2
(45) Date of Patent: Aug. 24, 2021

(54) MULTIVALENT HIV VACCINE BOOST COMPOSITIONS AND METHODS OF USE

(71) Applicant: GEOVAX INC., Smyrna, GA (US)

(72) Inventor: Harriet Robinson, Palo Alto, CA (US)

(73) Assignee: GEOVAX INC., Smyrna, GA (US)

(*) Notice: Subject to any disclaimer, the term of this patent is extended or adjusted under 35 U.S.C. 154(b) by 0 days.

(21) Appl. No.: 16/077,215

(22) PCT Filed: Feb. 16, 2017

(86) PCT No.: PCT/US2017/018103
§ 371 (c)(1),
(2) Date: Aug. 10, 2018

(87) PCT Pub. No.: WO2017/143016
PCT Pub. Date: Aug. 24, 2017

(65) Prior Publication Data
US 2019/0382453 A1 Dec. 19, 2019

Related U.S. Application Data

(60) Provisional application No. 62/295,779, filed on Feb. 16, 2016.

(51) Int. Cl.
*A61K 39/21* (2006.01)
*C07K 14/16* (2006.01)
*C12N 15/86* (2006.01)

(52) U.S. Cl.
CPC ........... *C07K 14/162* (2013.01); *A61K 39/21* (2013.01); *C12N 15/86* (2013.01); *C12N 2710/24143* (2013.01); *C12N 2740/16134* (2013.01)

(58) Field of Classification Search
CPC ................ C07K 14/162; A61K 39/21; A61K 2039/5258; C12N 15/86; C12N 2710/24143; C12N 2740/16134
See application file for complete search history.

(56) References Cited

U.S. PATENT DOCUMENTS

| 7,867,982 | B2 | 1/2011 | Moss et al. |
| 8,623,379 | B2 | 1/2014 | Robinson et al. |
| 8,916,172 | B2 | 12/2014 | Moss et al. |
| 9,254,319 | B2 | 2/2016 | Robinson et al. |
| 2004/0146528 | A1 | 7/2004 | Moss et al. |

FOREIGN PATENT DOCUMENTS

| WO | WO 2014/005958 | | 1/2014 |
| WO | WO 2015/009946 | | 1/2015 |
| WO | WO 2015/200673 | | 12/2015 |
| WO | WO 2015/200673 A2 | * | 12/2015 |
| WO | WO 2016/049287 | | 3/2016 |

OTHER PUBLICATIONS

Goepfert, P. A., et al., Jul. 2014, Specificity and 6-Month Durability of Immune Responses Induced by DNA and Recombinant Modified Vaccinia Ankara Vaccines Expressing HIV-1 Virus-Like Particles, J. Infect. Dis. 210:99-110.*
Cox, J. H., et al., 2012, Inclusion of a CRF01_AE HIV envelope protein boost with a DNA/MVA prime-boost vaccine: Impacton humoral and cellular immunogenicity and viral load reduction after SHIV-E challenge, Vaccine 30:1830-1840.*
Fouts, T. R., Mar. 2015, Balance of cellular and humoral immunity determines the level of protection by HIV vaccines in rhesus macaque models of HIV infection, Proc. Natl. Acad. Sci. E992-E999 (published online Feb. 13, 2015).*
International Search Report for PCT/US2017/018103, dated May 4, 2017.
Extended European Search Report from EP Patent Application No. 17753803.0, dated Oct. 17, 2019.
Goepfert, PA et al. Specificity and 6-Month Durability of Immune Responses Induced by DNA and Recombinant Modified Vaccinia Ankara Vaccines Expressing HIV-1 Virus-Like Particles. Jan. 7, 2014; vol. 210, No. 1; pp. 99-110.
Fouts, TR et al. Expression and Characterization of a Single-Chain Polypeptide Analogue of the Human Immunodeficiency Virus Type 1 gp120-CD4 Receptor Complex. Journal of Virology. Dec. 2000; vol. 74, No. 24; pp. 11427-11436.
Suzan L. Buge et al: "Gp120-Alum Boosting of a Gag-Pol-Env DNA/ MVA AIDS Vaccine: Poorer Control of a Pathogenic Viral Challenge", Aids Research and Human Retroviruses., vol. 19, No. 10, Oct. 1, 2003 (Oct. 1, 2003), pp. 891-900.
Smita S. Iyer et al: "Codelivery of Envelope Protein in Alum with MVA Vaccine Induces CXCR3-Biased CXCR5+ and CXCR5-CD4 T Cell Responses in Rhesus Macaques", The Journal of Immunology, vol. 195, No. 3, Jun. 26, 2015 (Jun. 26, 2015), pp. 994-1005.
Letvin N et al: "Potent, protective anti-HIV immune responses generated by bimodal HIV envelope DNA plus protein vaccination", Proceedings of the National Academy of Sciences (PNAS), vol. 94, Aug. 19, 1997 (Aug. 19, 1997), pp. 9378-9383.
Xiaoying Shen et al: "HIV gp120 and Modified Vaccinia Virus Ankara (MVA) gp140 Boost Immunogens Increase Immunogenicity of a DNA/MVA HIV-1 Vaccine", Journal of Virology., vol. 91, No. 24, Dec. 15, 2017.
Rerks-Ngarm S, et al., "Vaccination with ALVAC and AIDSVAX to Prevent HIV-1 Infection in Thailand," N Engl J Med. 361(23): 2209-20 (2009).

(Continued)

*Primary Examiner* — Jeffrey S Parkin
(74) *Attorney, Agent, or Firm* — Knowles Intellectual Property Strategies, LLC

(57) ABSTRACT

Compositions and methods of use are provided to boost a primed immune response to HIV. More specifically, the present invention relates to vaccine compositions comprising an HIV-protein boost or an MVA-expressed Env protein and methods of use. Exemplary HIV proteins for protein boosts include proteins such as gp120 proteins B.63521Δ11mutC and full-length single chain (FLSC), which has been modified to stabilize a CD4-induced Env structure. Exemplary MVAs expressing secreted Methods of administration and dosing regimens are also provided.

22 Claims, 9 Drawing Sheets

(56) References Cited

OTHER PUBLICATIONS

Buchbinder, S. P "Effi cacy assessment of a cell-mediated immunity HIV-1 vaccine (the Step Study): a double-blind, randomised, placebo-controlled, test-of-concept trial," Lancet 372, 1881-1893 (2008).
Duerr, A., et al. "Extended Follow-up Confirms Early Vaccine-Enhanced Risk of HIV Acquisition and Demonstrates Waning Effect Over Time Among Participants in a Randomized Trial of Recombinant Adenovirus HIV Vaccine (Step Study)," J Infect Dis 206, 258-266 (2012).
Fauci, A. S., "Immune Activation with HIV Vaccines," Science 344, 49-51 (2014).
Fouts T R, et al., "Balance of cellular and humoral immunity determines the level of protection by HIV vaccines in rhesus macaque models of HIV infection," 2015. Proc Natl Acad Sci USA doi: 10.1073/pnas.142366911.
Lewis G K, et al., "Antibody persistence and T-cell balance:Two key factors confronting HIV vaccine development," 2014, Proc Natl Acad Sci USA 111:15614-156210.
Douek D C, et al., "HIV preferentially infects HIV-specific CD41 Tcells," 2002, Nature 417:95-8.
Cox JH, Ferrari MG, Earl P, Lane JR, Jagodzinski LL, Polonis VR, et al. Inclusion of a CRF01_AE HIV envelope protein boost with a DNA/MVA prime-boost vaccine: Impact on humoral and cellular immunogenicity and viral load reduction after SHIV-E challenge. Vaccine. 2012;30(10):1830-40.
International Search Report from PCT Patent Application No. PCT/US2017/018103, dated Apr. 12, 2017.
Goepfert, PA et al.; Specificity and 6-Month Durability of Immune Responses Induced by DNA and Recombinant Modified Vaccinia Ankara Vaccines Expressing HIV-1 Virus-Like Particles. Jan. 7, 2014; vol. 210, No. 1; pp. 99-110; abstract; p. 100, col. 1, paragraphs 2-3.
Fouts, TR et al.; Expression and Characterization of a Single-Chain Polypeptide Analogue of the Human Immunodeficiency Virus Type 1 gp120-CD4 Receptor Complex. Journal of Virology. Dec. 2000; vol. 74, No. 24; pp. 11427-11436; abstract; figure 1; p. 11429, col. 1, paragraph 1.
Barouch, The Quest for an HIV-1 Vaccine—Moving Forward. NEJM 369;22 (2013).
ClinicalTrials.gov Identifier: NCT02852005—Evaluating the Immunogenicity of the AIDSVAX B/E Vaccine and the MVA/HIV62B Vaccine in Healthy, HIV-1-Uninfected Adults Who Previously Received MVA/HIV62B in DNA/MVA or MVA/MVA Regimens in HVTN 205.
Earl et al., Design and evaluation of multi-gene, multi-clade HIV-1 MVA vaccines. Vaccine 27 (2009) 5885-5895.
Experimental HIV Vaccine Regimen Ineffective in Preventing HIV No Safety Concerns Found; NIH and Partners Discontinue Vaccinations, Feb. 3, 2020, available at: https://www.niaid.nih.gov/news-events/experimental-hiv-vaccine-regimen-ineffective-preventing-hiv.
Flynn et al. Placebo-controlled phase 3 trial of a recombinant glycoprotein 120 vaccine to prevent HIV-1 infection. J Infect Dis 2005; 191:654-65.
Gray et al. Safety and efficacy of the HVTN 503/Phambili study of a clade-B-based HIV-1 vaccine in South Africa: a double-blind, randomised, placebo-controlled test-of-concept phase 2b study. Lancet Infect Dis 2011; 11:507-15.
Hammer et al. Efficacy trial of a DNA/rAd5 HIV-1 preventive vaccine. N Engl J Med 2013; 369:2083-92.
Haynes et al. Immune-correlates analysis of an HIV-1 vaccine efficacy trial. N Engl J Med 2012; 366:1275-86.
Pitisuttithum et al. Phase I/II study of a candidate vaccine designed against the B and E subtypes of HIV-1. J Acquir Immune Defic Syndr 2004; 37:1160-5.
Pitisuttithum et al. Randomized, double-blind, placebo-controlled efficacy trial of a bivalent recombinant glycoprotein 120 HIV-1 vaccine among injection drug users in Bangkok, Thailand. J. Infec Dis 2006; 194:1661-71.
Rerks-Ngarm et al. Randomized, Double-Blind Evaluation of Late Boost Strategies for HIV-Uninfected Vaccine Recipients in the RV144 HIV Vaccine Efficacy Trial. J Infect Dis 2017; 215:1255-63.

\* cited by examiner

FIG. 3A: Group median binding magnitude to linear epitopes

- ● MVA62B only
- ■ MVA62B + B.63521Δ11mutC + FLSC
- ▼ MVA62B + MVA-gp140

— MVA62B only
-■- MVA62B + B.63521Δ11mutC + FLSC
-▼- MVA62B + MVAgp140

MULTIVALENT HIV VACCINE BOOST COMPOSITIONS AND METHODS OF USE

CROSS REFERENCE TO RELATED APPLICATIONS

This application is a national stage application under 35 U.S.C. § 371 of International Application No. PCT/US2017/018103, filed Feb. 16, 2017, which claims the benefit of U.S. Provisional patent application 62/295,779 filed Feb. 16, 2016, the contents of which are hereby incorporated by reference in their entirety.

FIELD OF THE INVENTION

The present invention relates to compositions and methods of use to boost a primed immune response to HIV. More specifically, the present invention relates to boosting compositions comprising an MVA vector plus additional MVA vectors or HIV-proteins, as well as related methods of use.

BACKGROUND OF THE INVENTION

More than three decades after the discovery of HIV-1, AIDS remains a major public health problem affecting greater than 35.3 million people worldwide. In the absence of an approved vaccine, antiretroviral drugs are used for prophylactic and therapeutic purposes. Highly active antiretroviral therapy (HAART) is used to treat HIV-1 infection and impede development of AIDS, but HAART fails to adequately target the latently-infected cells that serve as a reservoir for HIV-1.

Clade B HIV is the most prevalent subtype of HIV in North America, western South America, Europe, Japan and Australia. Despite the effectiveness of pre-exposure and post-exposure prophylaxis in limiting HIV spread, the rate of new infections in the United States has been discouragingly constant for the past 20 years with 50-55,000 new infections per year. Only 25% of the estimated 1.2 million infections in the US are successfully controlled with antiretroviral agents (Hall, H. I., et al. AIDS 18, 81-88 (2004)). This low level of viral control results in infected individuals progressing more rapidly to AIDS and continuing to transmit the virus (Hall, H. I., et al. AIDS 18, 81-88 (2004), Porco, T. C., et al. AIDS 18, 81-88 (2004)). Particularly discouraging are the increasing rates of infection among youth aged 13-24. In male youth who have sex with men, HIV incidence rose by 132.5% between 2002 and 2011, or an average of 10.5% per year. The infection rate has become particularly high in certain geographic regions and at risk populations. In the Southeastern United States, for example, gay black men have a 40% chance of infection by the time they are 30 years old (Rosenberg, E., et al., Abstr. 38., Conference on Retroviruses and Opportunistic Infections, Boston, Mass. (2014). Clade B HIV is also at epidemic proportions in Peru where 12.5% of male homosexuals are infected and 56% of new infections are in male homosexuals (2012 UNAIDS, World AIDS Day Report).

The Clade B epidemic continues to be a major public health problem in the Americas. Costs of HIV care and treatment rose 37% from $12 billion in 2009 to just under $17 billion in 2014—a high and increasing burden for taxpayers (Kaiser Foundation Fact Sheet, June 2014). Financial costs, alone, demonstrate the critical need for a vaccine. Social costs of each HIV infection are also large, including patient time, lost productivity, and physical and emotional distress to patients and their families.

The landmark RV144 HIV vaccine clinical trial conducted in Thailand is one of the notable, yet still partial, successes in this field (Rerks-Ngarm S, et al., N Engl J Med. 361(23): 2209-20 (2009)). RV144 showed a modest (31%) ability to protect against HIV infection over the 3.5 years of the study. Further studies are being designed to improve the efficacy of the RV144vaccine.

Protein boosts using gp120 and gp140 for live-vectored HIV vaccines have uniformly boosted antibody responses, but had discordant results for boosting protection. For vaccines in which DNA has been used to prime a modified vaccinia Ankara (MVA) boost, gp120 and gp140 boosts have either decreased or failed to increase protection. (Buge, S. L et al., AIDS Res Hum Retroviruses 19, 891-900 (2003).; Iyer, S. S., *J Immunol* 195, 994-1005 (2015)). This failure to enhance protection has occurred for Alum, Adjuplex and 3M052-adjuvated gp120 and gp140 boosts. It has also occurred for trials in which the protein has been given simultaneously with the MVA boost, or the protein inoculations have followed the MVA boosts. In all of the DNA/MVA trials, the protein boosts have enhanced peak antibody responses. Thus, the protein boosts enhanced antibody responses, but the boosted responses were less effective than the non-boosted responses at providing protection.

It is possible that enhanced antibody responses decrease, or fail to enhance protection for DNA/MVA vaccines because protein boosts also could enhance CD4+ T cell responses that are targets for infection. HIV vaccines have a history of potentially enhancing susceptibility to infection (Buchbinder, S. P *Lancet* 372, 1881-1893 (2008); Duerr, A., et al. *J Infect Dis* 206, 258-266 (2012)), a phenomenon that is thought to reflect immune activation enhancing CD4+ T cells targets for infection (Fauci, A. S., *Science* 344, 49-51 (2014)).

Thus there remains a need for immunostimulatory compositions for HIV vaccines for prophylactic and therapeutic uses that induce robust and sustainable antibody responses without significantly enhancing CD4+ T cell responses that can increase susceptibility to infection. There remains a need for an effective vaccine for prophylactic and therapeutic use.

SUMMARY OF THE INVENTION

The present invention addresses the unmet need for an HIV vaccine to treat or prevent the worldwide HIV epidemic and particularly the clade B epidemic in the United States, Central and South America. The use of the particular components of boost composition described herein are useful for boosting antibody immune responses without significantly increasing CD4+ T cell responses. This property of the boost composition is important because enhanced CD4+ T cell responses may increase susceptibility to HIV infection and it is therefore desirable to generate a stable and durable antibody response without a substantial increase in CD4+ T cell response.

In a first aspect, the invention provides a boost composition that comprises i) a recombinant live virus (MVA vector) expressing membrane-bound HIV envelope protein associated with virus-like particles and ii) one or more additional HIV proteins.

In one embodiment, the MVA vector is MVA/HIV62B.

In one embodiment, the one or more additional HIV proteins are HIV envelope (Env) proteins.

In one embodiment, the HIV Env protein is native or mutant HIV gp120.

In one embodiment, the HIV Env protein is the B.63521Δ11mutC receptor-binding subunit of gp120.

In one embodiment, the HIV Env protein comprises the CD4-induced form of gp120.

In one embodiment, the CD4-induced form of the HIV Env protein is BAL gp120 fused to the D1D2 region of CD4 (full-length single chain (FLSC)).

In one embodiment, the HIV Env protein is native or mutant HIV gp140.

In a particular embodiment, the boost composition comprises i) an MVA vector expressing membrane-bound HIV envelope protein associated with virus-like particles and ii) the B.63521Δ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) an MVA-vector expressing a gp140.

In particular embodiments, the boost composition comprises i) an MVA vector expressing membrane-bound HIV envelope protein associated with virus-like particles and ii) two HIV envelope (Env) proteins selected from:
 a) B.63521Δ11mutC and FLSC,
 b) a gp120 and B.63521Δ11mutC,
 c) a gp120 and FLSC,
 d) a gp140 and B.63521Δ11mutC,
 e) a gp140 and FLSC, or
 f) a gp140 and a gp120.

In a particular embodiment, the boost composition comprises i) an MVA vector expressing membrane-bound HIV envelope protein associated with virus-like particles, ii) B.63521Δ11mutC receptor-binding subunit of gp120 and iii) FLSC, the CD4-induced form of gp120.

In one embodiment, the one or more additional HIV proteins are expressed from an MVA vector.

In one embodiment, the boost composition comprises a first MVA vector expressing membrane-bound HIV envelope protein associated with virus-like particles, and one or more additional MVA vectors expressing one or more HIV Env proteins.

In a second aspect, the invention provides a kit comprising: a first prime composition comprising at least one vector to induce an immune response to HIV and prime a patient's immune system; a first boost composition to boost the primed immune response, the boost composition comprising a combination of: i) an MVA vector expressing membrane-bound HIV envelope protein associated with virus-like particles and ii) one or more additional HIV proteins to boost the immune response.

In one embodiment, the first prime composition comprises a DNA vector expressing HIV antigens.

In one embodiment, the MVA vector is MVA/HIV62B.

In one embodiment, the one or more additional HIV proteins are HIV envelope (Env) proteins.

In one embodiment, the HIV Env protein is native or mutant HIV gp120.

In one embodiment, the HIV Env protein is the B.63521Δ11mutC receptor-binding subunit of gp120.

In one embodiment, the HIV Env protein comprises the CD4-induced form of gp120.

In one embodiment the HIV Env protein comprises FLSC.

In one embodiment, the HIV Env protein is native or mutant HIV gp140.

In a particular embodiment, the boost composition comprises i) an MVA vector expressing membrane-bound HIV envelope protein associated with virus-like particles and ii) the B.63521Δ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
 a) B.63521Δ11mutC and FLSC,
 b) a gp120 and B.63521Δ11mutC,
 c) a gp120 and FLSC,
 d) a gp140 and B.63521Δ11mutC,
 e) a gp140 and FLSC, or
 f) a gp140 and a gp120.

In a particular embodiment, the boost composition comprises i) an MVA vector expressing membrane-bound HIV envelope protein associated with virus-like particles, ii) B.63521Δ11mutC receptor-binding subunit of gp120 and iii) the full-length single chain (FLSC) of gp120.

In one embodiment, the one or more HIV proteins are expressed from an MVA vector.

In one embodiment, the boost composition comprises a first MVA vector expressing membrane-bound HIV envelope protein associated with virus-like particles, and one or more different MVA vector expressing one or more HIV Env proteins.

In a third aspect, the invention provides a method for inducing an immune response to HIV comprising administering to a subject in need thereof:
 1) a first composition to prime an immune response to HIV; and
 2) a second composition comprising a) an MVA vector expressing membrane-bound HIV envelope protein associated with virus-like particles and b) one or more additional HIV proteins to boost the immune response.

In one embodiment, the MVA vector is MVA/HIV62B.

In one embodiment, the one or more additional HIV proteins are HIV envelope (Env) proteins.

In one embodiment, the HIV Env protein is native or mutant HIV gp120.

In one embodiment, the HIV Env protein is the B.63521Δ11mutC receptor-binding subunit of gp120.

In one embodiment, the HIV Env protein comprises the full-length single chain (FLSC) CD4-induced form of gp120.

In one embodiment, the HIV Env protein is native or mutant HIV gp140.

In a particular embodiment, the boost composition comprises i) an MVA vector expressing membrane-bound HIV envelope protein associated with virus-like particles and ii) the B.63521Δ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
   a) B.63521Δ11mutC and FLSC,
   b) a gp120 and B.63521Δ11mutC,
   c) a gp120 and FLSC,
   d) a gp140 and B.63521Δ11mutC,
   e) a gp140 and FLSC, or
   f) a gp140 and a gp120.

In a particular embodiment, the boost composition comprises i) an MVA vector expressing membrane-bound HIV envelope protein associated with virus-like particles, ii) B.63521Δ11mutC receptor-binding subunit of gp120 and iii) the full-length single chain (FLSC) CD4-induced form of gp120.

In one embodiment, the one or more additional HIV proteins are expressed from an MVA vector.

In one embodiment, the boost composition comprises a first MVA vector expressing membrane-bound HIV envelope protein associated with virus-like particles, and one or more additional MVA vector expressing one or more additional HIV Env proteins.

In one embodiment, the prime composition is administered about 8 weeks apart.

In one embodiment, the prime composition is administered at about week 0 and 8.

In one embodiment, the boost composition is administered about 8 weeks after one or more priming composition administration.

In one embodiment, the boost composition is administered at least 2 times.

In one embodiment, the boost composition is administered about 3 times.

In one embodiment, the boost composition is administered at about week 16, 24 and 40 after administration of one or more priming compositions.

In one embodiment, the boost composition is administered at about week 8, 16 and 32 after one or more priming compositions.

In a fourth aspect, the invention provides a method for boosting a primed immune response to HIV comprising administering to a subject in need thereof:
   1) a first composition to prime an immune response to HIV; and
   2) a second composition comprising a) an MVA vector expressing HIV envelope protein associated with virus-like particles and b) one or more additional HIV proteins to boost the immune response.

In one embodiment, the first prime composition comprises a DNA vector expressing HIV antigens.

In one embodiment, the MVA vector is MVA/HIV62B.

In one embodiment, the one or more additional HIV proteins are HIV envelope (Env) proteins.

In one embodiment, the HIV Env protein is native or mutant HIV gp120.

In one embodiment, the HIV Env protein is the B.63521Δ11mutC receptor-binding subunit of gp120.

In one embodiment, the HIV Env protein comprises the full-length single chain (FLSC) CD4-induced form of gp120.

In one embodiment, the HIV Env protein is native or mutant HIV gp140.

In a particular embodiment, the boost composition comprises i) an MVA vector expressing membrane-bound HIV envelope protein associated with virus-like particles and ii) the B.63521Δ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
   a) B.63521Δ11mutC and FLSC,
   b) a gp120 and B.63521Δ11mutC,
   c) a gp120 and FLSC,
   d) a gp140 and B.63521Δ11mutC,
   e) a gp140 and FLSC, or
   f) a gp140 and a gp120.

In a particular embodiment, the boost composition comprises i) an MVA vector expressing membrane-bound HIV envelope protein associated with virus-like particles, ii) B.63521Δ11mutC receptor-binding subunit of gp120 and iii) the full-length single chain (FLSC) CD4-induced form of gp120.

In one embodiment, the one or more additional HIV proteins are expressed from an MVA vector.

In one embodiment, the boost composition comprises a first MVA vector expressing membrane-bound HIV envelope protein associated with virus-like particles, and one or more different MVA vector expressing one or more additional HIV Env proteins.

In one embodiment, the prime composition is administered about 8 weeks apart.

In one embodiment, the prime composition is administered at about week 0 and 8.

In one embodiment, the boost composition is administered about 8 weeks after the last priming composition administration.

In one embodiment, the boost composition is administered at least 2 times.

In one embodiment, the boost composition is administered about 3 times.

In one embodiment, the boost composition is administered at about week 16, 24 and 40 after administration of the first priming composition.

In one embodiment, the boost composition is administered at about week 8, 16 and 32 after the last priming composition.

In a fifth aspect, the invention provides a method of priming and boosting an immune response to HIV comprising administering to a subject in need thereof in an effective amount:
   a composition to induce and boost an immune response to HIV wherein the composition comprises: i) a first MVA vector expressing membrane-bound HIV envelope protein associated with virus-like particles, and ii) at least one additional HIV protein.

In one embodiment, the MVA vector is MVA/HIV62B.

In one embodiment, the one or more additional HIV proteins are HIV envelope (Env) proteins.

In one embodiment, the HIV Env protein is native or mutant HIV gp120.

In one embodiment, the HIV Env protein is the B.63521Δ11mutC receptor-binding subunit of gp120.

In one embodiment, the HIV Env protein comprises the full-length single chain (FLSC) CD4-induced form of gp120.

In one embodiment, the HIV Env protein is native or mutant HIV gp140.

In a particular embodiment, the boost composition comprises i) an MVA vector expressing membrane-bound HIV envelope protein associated with virus-like particles and ii) the B.63521Δ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
 a) B.63521Δ11mutC and FLSC,
 b) a gp120 and B.63521Δ11mutC,
 c) a gp120 and FLSC,
 d) a gp140 and B.63521Δ11mutC,
 e) a gp140 and FLSC, or
 f) a gp140 and a gp120.

In a particular embodiment, the boost composition comprises i) an MVA vector expressing membrane-bound HIV envelope protein associated with virus-like particles, ii) B.63521Δ11mutC receptor-binding subunit of gp120 and iii) the full-length single chain (FLSC) CD4-induced form of gp120.

In one embodiment, the one or more HIV proteins are expressed from an MVA vector.

In one embodiment, the boost composition comprises a first MVA vector expressing membrane-bound HIV envelope protein associated with virus-like particles, and one or more additional MVA vector expressing one or more HIV Env proteins.

In one embodiment, the composition is administered about 3 times.

In one embodiment, the boost composition is administered at about 8 to 16 weeks apart.

BRIEF DESCRIPTION OF THE DRAWINGS

FIG. 1A and FIG. 1B: Group median IgG binding magnitude for Con6 gp120 (FIG. 1A) and MN gp41 (FIG. 1B) of longitudinal sera measured in ELISA. Dotted vertical lines indicate time of immunizations. D—DNA prime at weeks 0 and 8. M—MVA boost at weeks 18, 26, and 40. FIG. 1C to FIG. 1F provide graphs showing Mean median fluorescent intensity (MFI) for binding to the gp120 (FIG. 1C), gp140 (FIG. 1D), or V1V2 (FIG. 1E) antigen reference panels measured in binding antibody multiplex assays (BAMA), or mean intensity of binding to 13 V3 peptides measured in linear epitope mapping (FIG. 1F). MFI for gp120 and gp140 antigens were obtained from 1:400 plasma dilutions. MFI for V1V2 antigens were obtained from 1:80 plasma dilutions. Intensities for binding to V3 peptides were obtained from 1:50 plasma dilutions. Each symbol represents binding by one plasma sample to one antigen panel. Shaded columns represent group median values and bars represent interquartile ranges. * indicates p<0.05 for pair wise comparison (exact Wilcoxon rank sum). FIG. 1C-1F. Key to boosts: MVA-only, filled square, MVA+gp120, triangle; MVA+gp140, upside down triangle FIG. 2 provides figures showing contraction (FIG. 2A) and fold boost (FIG. 2B) of binding responses for 3 antigen panels in GV-M1. Contraction was calculated as wk28/wk40 mean MFI binding to the antigen panel. Fold of boost was calculated as wk42/wk28 mean MFI binding to the antigen panel. Each symbol represents the calculated ratio for each sample. Error bars represent group medians and interquartile ranges. * indicates p<0.05 and ** p<0.01 for pair wise comparison (exact Wilcoxon rank sum). Key to boosts: MVA-only, filled circles; MVA+gp120, filled squares, MVA+MVA-gp140, triangle FIG. 3 provides schematics showing the proportions of total linear binding to each identified epitope (FIG. 3 A) or to each strain included in the epitope mapping peptide library (FIG. 3 B) in GV-M1. Each sector in panel A represents a group median magnitude to an epitope, which was calculated as the highest binding to a single peptide within each epitope region. Each sector in panel B represents a group median total linear epitope binding for a strain, which was calculated as the sum of binding intensities to all linear peptides for that strain.

DETAILED DESCRIPTION OF THE INVENTION

Figure 1A:
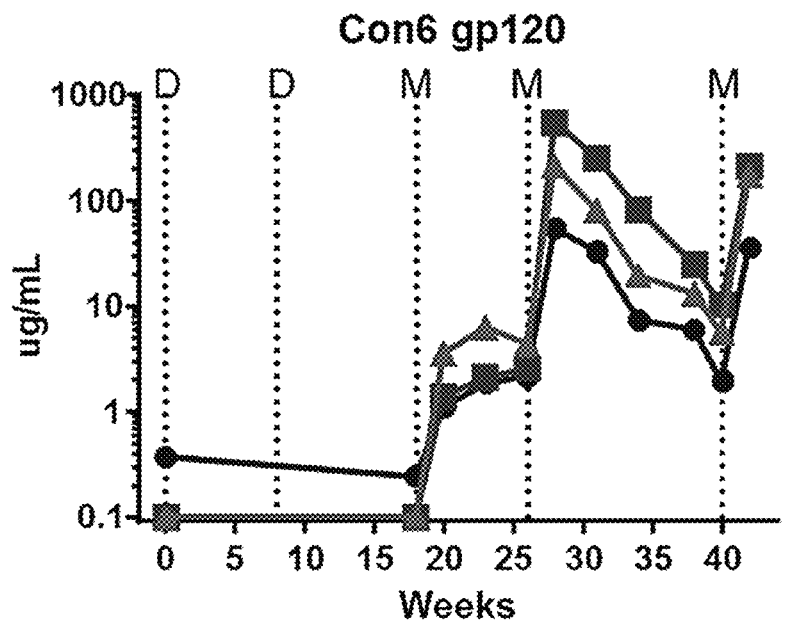
FIG. 1A to FIG. 1F provide graphs showing the magnitude of binding antibody responses in trial GV-M1 in rhesus macaques.

The present invention provides peptide and vector compositions useful for boosting a primed immune response to HIV as well as methods for inducing an immune response utilizing the same in order to treat or prevent HIV infection. The peptide compositions include one or more HIV proteins expressed by a vector or mutated or unmutated subunits from different Env proteins. The particular components of the boost compositions described herein are useful for boosting antibody immune responses to Env including the V1V2 and V3 loops of gp120 and the CD4-induced form of gp120 without necessarily increasing CD4+ T cell responses. This property of the boost composition is important because enhanced T cell responses may increase susceptibility to HIV infection as a result of inoculation and it is therefore desirable to generate a stable and durable antibody response without a substantial increase in T cell response.

I. DEFINITIONS

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a peptide" includes a plurality of peptides. Thus, for example, a reference to "a method" includes one or more methods, and/or steps of the type described herein and/or which will become apparent to those persons skilled in the art upon reading this disclosure.

The term "administer", "administering" or "administered" means refers to the act of giving an agent or therapeutic treatment to a physiological system (e.g., a subject or in vivo, in vitro, or ex vivo cells, tissues, and organs).

The term "antigen" refers to a substance or molecule, such as a protein, or fragment thereof, that is capable of inducing an immune response.

The term "binding antibody" or "bAb" refers to an antibody which either is purified from, or is present in, a body fluid (e.g., serum or a mucosal secretion) and which recognizes a specific antigen. As used herein, the antibody can be a single antibody or a plurality of antibodies. Binding antibodies comprise neutralizing and non-neutralizing antibodies.

The term "cell-mediated immune response" refers to the immunological defense provided by lymphocytes, such as the defense provided by sensitized T cell lymphocytes when they directly lyse cells expressing foreign antigens and secrete cytokines (e.g., IFN-gamma.), which can modulate macrophage and natural killer (NK) cell effector functions and augment T cell expansion and differentiation. The cellular immune response is the $2^{nd}$ branch of the adaptive immune response.

The term "conservative amino acid substitution" refers to substitution of a native amino acid residue with a non-native residue such that there is little or no effect on the size, polarity, charge, hydrophobicity, or hydrophilicity of the amino acid residue at that position, and without resulting in substantially altered immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

As used herein, the term "effective amount" refers to the amount of a therapy (e.g. a prophylactic or therapeutic agent) which is sufficient to effect beneficial or desired results, including clinical results. An effective amount can be administered in one or more administrations.

The term "humoral immune response" refers to the stimulation of antibody production. Humoral immune response also refers to the accessory proteins and events that accompany antibody production, including T helper cell activation and cytokine production, affinity maturation, and memory cell generation. The humoral immune response is one of the two branches of the adaptive immune response.

The term "humoral immunity" refers to the immunological defense provided by antibody, such as neutralizing antibodies that can directly block infection; or, binding antibodies that identifies a virus or infected cell for killing by such innate immune responses as complement (C')-mediated lysis, phagocytosis, and natural killer cells.

The term "immune response" refers to any response to an antigen or antigenic determinant by the immune system of a subject (e.g., a human). Exemplary immune responses include humoral immune responses (e.g., production of antigen-specific antibodies) and cell-mediated immune responses (e.g., production of antigen-specific T cells).

The term "improved therapeutic outcome" relative to a subject diagnosed as infected with a particular virus (e.g., HIV) refers to a slowing or diminution in the growth of virus, or viral load, or detectable symptoms associated with infection by that particular virus; or a reduction in the ability of the infected subject to transmit the infection to another, uninfected subject.

The term "inducing an immune response" means eliciting a humoral response (e.g., the production of antibodies) or a cellular response (e.g., the activation of T cells) directed against a virus (e.g., HIV) in a subject to which the composition (e.g., a vaccine) has been administered.

The term "insertion" in the context of a polypeptide or protein refers to the addition of one or more non-native amino acid residues in the polypeptide or protein sequence. Typically, no more than about from 1 to 6 residues (e.g. 1 to 4 residues) are inserted at any one site within the polypeptide or protein molecule.

The term "modified vaccinia Ankara," "modified vaccinia ankara," "Modified Vaccinia Ankara," or "MVA" refers to a highly attenuated strain of vaccinia virus developed by serial passage on chick embryo fibroblast cells; or variants or derivatives thereof. MVA is reviewed in (Mayr, A. et al. 1975 Infection 3:6-14; Swiss Patent No. 568,392).

The term "neutralizing antibody" or "NAb" is meant as an antibody which either is purified from, or is present in, a body fluid (e.g., serum or a mucosal secretion) and which recognizes a specific antigen and inhibits the effect(s) of the antigen in the subject (e.g., a human). As used herein, the antibody can be a single antibody or a plurality of antibodies.

The term "non-neutralizing antibody" or "nnAb" refers to a binding antibody that is not a neutralizing antibody.

The term "pharmaceutically acceptable carrier" refers to any such carriers known to those skilled in the art to be suitable for the particular mode of administration. For example, the term "pharmaceutically acceptable carrier" includes any and all solvents, dispersion media, coatings, antibacterial and antifungal agents, isotonic and absorption delaying agents and the like, that may be used as a media for a pharmaceutically acceptable substance. In addition, the active materials can also be mixed with other active materials that do not impair the desired action, or with materials that supplement the desired action, or have another action.

The term "prevent", "preventing" and "prevention" refers to the inhibition of the development or onset of a condition (e.g., a HIV infection or a condition associated therewith), or the prevention of the recurrence, onset, or development of one or more symptoms of a condition in a subject resulting from the administration of a therapy or the administration of a combination of therapies.

The term "prophylactically effective amount" refers to the amount of a composition (e.g., the recombinant MVA vector or pharmaceutical composition) which is sufficient to result in the prevention of the development, recurrence, or onset of a condition or a symptom thereof (e.g., HIV infection or a condition or symptom associated therewith or to enhance or improve the prophylactic effect(s) of another therapy.

The term "subject" means any mammal, including but not limited to, humans, domestic and farm animals, and zoo, sports, or pet animals, such as dogs, horses, cats, cows, rats, mice, guinea pigs and the like.

The term "surrogate endpoint" means a clinical measurement other than a measurement of clinical benefit that is used as a substitute for a measurement of clinical benefit.

The term "surrogate marker" means a laboratory measurement or physical sign that is used in a clinical or animal trial as a substitute for a clinically meaningful endpoint that is a direct measure of how a subject feels, functions, or survives and is expected to predict the effect of the therapy (Katz, R., NeuroRx 1:189-195 (2004); New drug, antibiotic, and biological drug product regulations; accelerated approval—FDA. Final rule. Fed Regist 57: 58942-58960, 1992.)

The term "surrogate marker for protection" means a surrogate marker that is used in a clinical or animal trial as a substitute for the clinically meaningful endpoint of prevention of HIV infection.

The term "synonymous codon" refers to the use of a codon with a different nucleic acid sequence to encode the same amino acid, e.g., AAA and AAG (both of which encode lysine). Codon optimization changes the codons for a protein to the synonymous codons that are most frequently used by a vector or a host cell.

The term "therapeutically effective amount" means the amount of the composition (e.g., the recombinant MVA vector or pharmaceutical composition) that, when administered to a mammal for treating an infection, is sufficient to affect such treatment for the infection.

As used herein, the terms "treat", "treatment" and "treating" refer to the prevention, reduction or amelioration of the progression, severity, and/or duration of at least one symptom of any condition or disease such as HIV infection. The term "treatment" or "treating" refers to any administration of a compound of the present invention and includes (i) inhibiting the disease, or the disease state in an individual that is experiencing or displaying the pathology or symptomatology of the disease, or the disease state (i.e., arresting further development of the pathology and/or symptomatology) or (ii) ameliorating the disease in an individual that is experiencing or displaying the pathology or symptomatology of the disease, or the disease state (i.e., reversing the pathology and/or symptomatology). The term "controlling" includes preventing, treating, eradicating, ameliorating or otherwise reducing the severity of symptoms of the disease, or the disease state.

As used herein relating to generating an immune response, the term "therapeutically effective amount" refers to that amount of a therapy, which is sufficient to induce or boost an immune response to HIV or improve the therapeutic effect (s) of another therapy (e.g., a prophylactic or therapeutic agent). A therapeutically effective amount can be administered in one or more administrations.

The term "vaccine" means material used to provoke an immune response and confer immunity after administration of the material to a subject. Such immunity may include a cellular or humoral immune response that occurs when the subject is exposed to the immunogen after vaccine administration.

The term "vaccine insert" refers to a nucleic acid sequence encoding a heterologous sequence that is operably linked to a promoter for expression when inserted into a recombinant vector. The heterologous sequence may encode an HIV antigen or structural protein described here.

The term "viral infection" means an infection by a viral pathogen (e.g., HIV) wherein there is clinical evidence of the infection based on symptoms or based on the demonstration of the presence of the viral pathogen in a biological sample from the subject.

The term "virus-like particles" or "VLP" refers to a structure which resembles the native virus antigenically and morphologically.

II. HIV VECTOR PRIME COMPOSITIONS

HIV vaccine compositions useful in the present invention include those compositions comprising DNA and/or MVA vectors expressing HIV antigens that prime and/or boost an immune response to HIV. In some embodiments, the HIV antigens are modified to provide safe non-infectious virus-like particles capable of priming an immune response to HIV. Examples of such compositions include DNA vectors that express HIV antigens, MVA vectors that express HIV antigens and combination thereof to prime an immune response to HIV. Exemplary vectors are disclosed in U.S. Pat. No. 8,623,379 and U.S. Patent Publication US 20080193483 the contents of which are herein incorporated by reference in their entirety.

DNA Vectors

Several plasmids have been previously constructed and used to express HIV antigens (U.S. Pat. No. 8,623,379). The plasmids made and used include pGA1 and its derivatives pGA1.1 and pGA1.2; and pGA2, and its derivatives pGA2.1 and pGA2.2. The vaccine constructs are typically referred to with the "backbone" vector and the "insert" being separated by a backslash. These constructs express HIV-1 antigens, and those constructs can be administered to patients as described herein. Plasmids containing JS7-like inserts appear to exhibit better immunogenicity and are more efficient in priming an immune response (as evidenced by anti-Env antibodies) pGA2/JS7 and pGA2/JS7.1 differ from pGA2/JS2 in several ways, one of which is the source of their respective antigens. In pGA2/JS7 and pGA2/JS7.1, the Gag gene was obtained from HIV-1 HXB2 and the pol gene from HIV-1-BH10, whereas in pGA2/JS2 those genes were obtained from HIV-1-BH10. Moreover, these inserts can contain mutations that inhibit one or more of the biological activities carried out by Gag-Pol. The vaccine inserts designated JS7 and JS2 also differ in that JS7 has an inactivating point mutation in its protease gene. This mutation facilitates the formation of viral like particles (VLPs). While not to be bound by any theory, it is believed that the mutation precludes premature intracellular cleavage of the overexpressed pr55 Gag protein. pGA2/JS7 and pGA2/JS7.1 both contain this protease mutation and both constructs produce VLPs in abundance. Accordingly, inserts that include mutant gag and/or pol sequences (e.g., one or more deletions or point mutations that inhibit protease function) are a preferred prime embodiment. Additional point mutations in the vpu gene in pGA2/JS7.1 resulted in a loss of Vpu expression and an increase in Env expression (in pGA2/JS7.1, the start site of Vpu is mutated along with a downstream ATG to eliminate translation of Vpu). The increase in Env expression does not compromise Gag expression.

Where the composition includes a vector with an insert, that encodes multiple protein antigens, one of the antigens can be a wild type or mutant gag sequence, including those described above. Similarly, where a composition includes more than one type of vector with more than one type of insert, at least one of the inserts (whether encoding a single antigen or multiple antigens) can include a wild type or mutant gag sequence, including those described above or analogous sequences from other HIV clades. For example, where the composition includes first and second vectors, the vaccine insert in either or both vectors (whether the insert encodes single or multiple antigens) can encode Gag; where both vectors encode Gag, the Gag sequence in the first vector can be from one HIV clade (e.g., clade B) and that in the second vector can be from another HIV clade (e.g., clade C).

Where the composition includes a vector with an insert that encodes a single antigen, the antigen can be wild type or mutant Pol. The sequence can be mutated by deleting or replacing one or more nucleic acids, and those deletions or substitutions can result in a Pol gene product that has less enzymatic activity than its wild type counterpart (e.g., less integrase activity, less reverse transcriptase (RT) activity, less strand-transfer activity or less protease activity). Nucleic acids encoding analogous residues in other HIV clades can be identified by one of ordinary skill in the art, even if those residues are not found at precisely the same position as they were in the clades tested here.

Where a composition includes more than one type of vector with more than one type of insert, at least one of the vectors with an insert (whether encoding a single antigen or multiple antigens) can include a wild type or mutant pol sequence, including those described above (and, optionally, a wild type or mutant gag sequence, including those described above (i.e., the inserts can encode Gag-Pol)). For example, where the composition includes first and second vectors, the vaccine insert in either or both vectors (whether the insert encodes single or multiple antigens) can encode Pol; where both vectors encode Pol, the Pol sequence in the first vector can be from one HIV clade (e.g., clade B) and that in the second vector can be from another HIV clade (e.g., clade AG).

Where an insert includes some or all of the pol sequence, another portion of the pol sequence that can be altered is the sequence encoding the protease activity (regardless of whether or not sequences affecting other enzymatic activities of Pol have been altered).

Where the composition includes either a vector with an insert and that insert encodes a single antigen, the antigen can be a wild type or mutant Env, Tat, Rev, Nef, Vif, Vpr, or Vpu. Where the composition includes a vector with an insert and that insert encodes multiple protein antigens, one of the antigens can be a wild type or mutant Env. For example, multi-protein expressing inserts can encode wild type or mutant Gag-Pol and Env; they can also encode wild type or mutant Gag-Pol and Env and one or more of Tat, Rev, Nef, Vif, Vpr, or Vpu (each of which can be wild type or mutant). As with other antigens, Env, Tat, Rev, Nef, Vif, Vpr, or Vpu can be mutant by virtue of a deletion, addition, or substitution of one or more amino acid residues (e.g., any of these antigens can include mutations). With respect to Env, one or more mutations can be in any of the known domains. For example, one or more amino acids can be deleted or substituted from the gp120 surface and/or gp41 transmembrane cleavage products. With respect to Gag, one or more amino acids can be deleted or substituted from one or more of: the matrix protein (p17), the capsid protein (p24), the nucleocapsid protein (p7) and the C-terminal peptide (p6). For example, amino acids in one or more of these regions can be deleted or substituted (this may be especially desired where the vector is a viral vector, such as MVA).

More specifically, the compositions of the invention can include a vector (e.g., a plasmid or viral vector) that encodes: (a) a Gag protein in which one or more of the zinc fingers has been inactivated to limit the packaging of viral RNA; (b) a Pol protein in which (i) the integrase activity has been inhibited by deletion of some or all of the pol sequence and (ii) the polymerase, strand transfer and/or RNase H activity of reverse transcriptase has been inhibited by one or more point mutations within the pol sequence; and (c) Env, Tat, Rev, and Vpu, with or without mutations. In this embodiment, as in others, the encoded proteins can be obtained or derived from a subtype A, B or C HIV (e.g., HIV-1) or recombinant forms thereof. Where the compositions include non-identical vectors, the sequence in each type of vector can be from a different HIV clade (or subtype or recombinant form thereof). For example, the invention features compositions that include plasmid vectors encoding the antigens just described (Gag-Pol, Env etc.), where some of the plasmids include antigens that are obtained from, or derived from, one clade and other plasmids include antigens that are obtained (or derived) from another clade. Mixtures representing two, three, four, five, six, or more clades (including all clades) are also contemplated.

The compositions of the invention can also include a vector (e.g., a plasmid vector) encoding: (a) a Gag protein in which one or both zinc fingers have been inactivated; (b) a Pol protein in which (i) the integrase activity has been inhibited by deletion of some or all of the pol sequence, (ii) the polymerase, strand transfer and/or RNase H activity of reverse transcriptase have been inhibited by one or more point mutations within the pol sequence and (iii) the proteolytic activity of the protease has been inhibited by one or more point mutations; and (c) Env, Tat, Rev, and Vpu, with or without mutations. As noted above, proteolytic activity can be inhibited by introducing a mutation in the sequence of other HIV clades. For example, the plasmids can contain the inserts described as JS7, IC25, and IN3 (U.S. Pat. No. 8,623,379). As is true for plasmids encoding other antigens, plasmids encoding the antigens just described can be combined with (e.g., mixed with) other plasmids that encode antigens obtained from, or derived from, a different HIV clade (or subtype or recombinant form thereof). The inserts per se (sans vector) are also within the scope of the invention.

Where first and second vectors are included in a composition, either vector can be pGA1/JS2, pGA1/JS7, pGA1/JS7.1, pGA2/JS2, pGA2/JS7, pGA2/JS7.1 (pGA1.1 can be used in place of pGA1 and pGA2.1 or pGA2.2 can be used in place of pGA2). Similarly, either vector can be pGA1/IC25, pGA1/IC2, pGA1/IC48, pGA1/IC90, pGA2/IC25, pGA2/IC2, pGA2/IC48, or pGA2/IC90 (here again, pGA1.1 or pGA1.2 can be used in place of pGA1 and pGA2.1 or pGA2.2 can be used in place of pGA2). In alternative embodiments, the encoded proteins can be those of, or those derived from, a subtype C HIV (e.g., HIV-1) or a recombinant form thereof. For example, the vector can be pGA1/IN2, pGA1.1/IN2, pGA1.2/IN2, pGA1/IN3, pGA1.1/IN3, pGA1.2/IN3, pGA2/IN2, pGA2.1 pGA2.2/IN2, pGA2/IN3, pGA2.1/IN3, or pGA2.2/IN3. Methods of making these vectors are described in U.S. Pat. No. 8,623,379.

In one embodiment, the DNA vector expresses virus like particles that display membrane-bound HIV envelope protein.

In one particular embodiment, the DNA vector is a pGA2/JS7 vaccine plasmid. (U.S. Pat. No. 8,623,379)

TABLE 1 pGA2/JS7 Functional Regions

| Position within sequence (starting and ending pos.) | Gene/ORF (indicate complete name of the gen and the expressed gene product) | Origin of sequence (organism) |
|---|---|---|
| 106-1608 | Gag, inactivating point mutations in zinc finger packaging sequences for viral RNA | HIV-1 HXB2 |
| 1401-3584 | Pol, inactivating point mutations in reverse transcriptase, deletion of integrase | HIV-1 HXB2 |
| 3671-3885 and 6210-6300 | Tat exons #1 and #2 | |
| 3810-3885 and 6210-6884 | Rev exons #1 and #2 | |
| 3902-4147 | Vpu | |
| 4165-6626 | Env | HIV-ADA |
| 6627-9506 | Plasmid vector | pGA2, GenBank accession # AF425298 |

TABLE 2 pGA2/JS7 Mutation Chart

| Codon Change | Amino acid change | Region | Function |
|---|---|---|---|
| to AGC Position 1279-1281 | C392S | Gag | Ablation of zinc finger used in packaging |
| to AGC Position 1288-1290 | C395S | Gag | Ablation of zinc finger used in packaging |
| to AGC Position 1342-1344 | C413S | Gag | Ablation of zinc finger used in packaging |
| to AGC Position 1351-1353 | C416S | Gag | Ablation of zinc finger used in packaging |
| to ACA Position 1641-1643 | D25A | Protease | Inactivation of Protease active site |
| to AAC Position 2418-2420 | D185N | Reverse Transcriptase | Inactivation of Polymerase active site |
| to ACC Position 2661-2663 | W266T | Reverse Transcriptase | Ablation of strand transfer activity |
| to CAG Position 3297-3299 | E478Q | RNase H | Inactivation of RNase H activity |

In one particular embodiment, the DNA vector is a pGA2/JS7.1 vaccine plasmid. (U.S. Pat. No. 8,623,379)

TABLE 3 pGA2/JS7.1 Functional Regions

| Position within sequence (starting and ending pos.) | Gene/ORF (indicate complete name of the gen and the expressed gene product) | Origin of sequence (organism) |
|---|---|---|
| 106-1608 | Gag, inactivating point mutations in zinc finger packaging sequences for viral RNA | HIV-1 HXB2 |
| 1401-3584 | Pol, inactivating point mutations in reverse transcriptase, deletion of integrase | HIV-1 HXB2 |
| 3671-3885 and 6210-6300 | Tat exons #1 and #2 | HIV-1 ADA |
| 3810-3885 and 6210-6884 | Rev exons #1 and #2 | HIV-1 ADA |
| 3902-4147 | Vpu start site mutated (G3904C) and upstream ATG mutated (G3899C) | HIV-1 ADA |
| 4165-6626 | Env | HIV-1 ADA |
| 6627-9506 | Plasmid vector | pGA2, GenBank accession # AF42598 |

TABLE 4 pGA2/JS7.1 Mutation Chart

| Codon Change | Amino acid change | Region | Function |
|---|---|---|---|
| to AGC Position 1279-1281 | C392S | Gag | Ablation of zinc finger used in packaging |
| to AGC Position 1288-1290 | C395S | Gag | Ablation of zinc finger used in packaging |
| to AGC Position 1342-1344 | C413S | Gag | Ablation of zinc finger used in packaging |
| to AGC Position 1351-1353 | C416S | Gag | Ablation of zinc finger used in packaging |
| to ACA Position 1641-1643 | D25A | Protease | Inactivation of Protease active site |
| to AAC Position 2418-2420 | D185N | Reverse Transcriptase | Inactivation of Protease active site |
| to ACC Position 2661-2663 | W266T | Reverse Transcriptase | Ablation of strand transfer activity |
| to CAG Position 3297-3299 | E478Q | RNase H | Inactivation of RNase H activity |
| to ATC Position 3902-3904 | NA | Vpu | Vpu start site mutated |
| to ATC Position 3897-3899 | NA | Non-coding region | ATG upstream of Vpu mutated |

III. HIV BOOST COMPOSITIONS

A. MVA Vector Boosts

Vaccinia virus, a member of the genus Orthopoxvirus in the family of Poxviridae, was used as a live vaccine to immunize against the human smallpox disease. Successful worldwide vaccination with vaccinia virus culminated in the eradication of variola virus, the causative agent of smallpox ("The global eradication of smallpox. Final report of the global commission for the certification of smallpox eradication". History of Public Health, No. 4, Geneva: World Health Organization, 1980). Since that WHO declaration, vaccination has been universally discontinued except for people at high risk of poxvirus infections (e.g. laboratory workers).

Vaccinia viruses have also been used to engineer viral vectors for recombinant gene expression and for the potential use as recombinant live vaccines (Mackett, M. et al 1982 PNAS USA 79:7415-7419; Smith, G. L. et al. 1984 Biotech Genet Engin Rev 2:383-407). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect cells and thus to express the integrated DNA sequence (EP Patent Applications No. 083,286 and No. 110,385). The recombinant vaccinia viruses prepared in this way can be used, on the one hand, as live vaccines for the prophylaxis of infectious diseases, on the other hand, for the preparation of heterologous proteins in eukaryotic cells.

In one embodiment, the MVA vector is a particular modified vaccinia virus Ankara (MVA) recombinant virus, (referred to herein as MVA/HIV62B), that expresses clade B HIV strains ADA Env and chimeric HXB2/BH10 Gag Pol. The env gene is inserted into del II of MVA genome and the gag pol is inserted in del III. Both env and gag pol of MVA/HIV 62B are controlled by the early-late promoter, PmH5. The MVA virus used to make the recombinant MVA/HIV 62B is MVA 1974/NIH Clone 1. The clade B gag pol was truncated so that the integrase was removed and was cloned into the plasmid so that it was controlled by the mH5 promoter. This gene contained the complete HXB2 sequence of the gag. The pol gene (largely from BH10) has reverse transcriptase safety mutations in amino acid 185 within the active site of RT, in amino acid 266 which inhibits strand transfer activity, and at amino acid 478 which inhibits the RNase H activity. In addition, the integrase gene is deleted past the EcoRI site. The ADA envelope is a truncated version with silent 5TNT mutations. The envelope was truncated in the cytoplasmic tail of the gp41 gene, deleting 115 amino acids of the cytoplasmic tail. This truncation increases the amount of envelope protein on the surface of infected cells and enhances immunogenicity of the envelope protein in mice, and the stability of the recombinant virus in tissue culture.

In various embodiments, the boost composition comprises an MVA vector that expresses HIV antigens.

In one embodiment, the boost composition comprises MVA vector MVA/HIV62B, a vector that expresses virus like particles that display membrane bound Env.

Methods of making this MVA vector are described in US Patent Publication 20080193483.

In one embodiment, the boost composition comprises i) a first MVA vector that expresses membrane-bound HIV envelope protein associated with virus-like particles, and ii) one or more additional MVA vector that express one or more additional HIV proteins.

In one embodiment, the first MVA vector is MVA/HIV62B.

In one embodiment, the one or more HIV proteins are expressed from an MVA vector.

In one embodiment, the one or more HIV proteins are envelope (Env) proteins.

In one embodiment, the HIV Env protein is native or mutant HIV gp120.

In one embodiment, the HIV Env protein is the B.63521Δ11mutC receptor-binding subunit of gp120.

In one embodiment, the HIV Env protein peptides comprise the full-length single chain (FLSC) CD4-induced form of gp120.

In one embodiment, the HIV Env protein is native or mutant HIV gp140.

In a particular embodiment, the boost composition comprises i) an MVA vector expressing membrane-bound HIV envelope protein associated with virus-like particles and ii) the B.63521Δ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
  a) B.63521Δ11mutC and FLSC,
  b) a gp120 and B.63521Δ11mutC,
  c) a gp120 and FLSC,
  d) a gp140 and B.63521Δ11mutC,
  e) a gp140 and FLSC, or
  f) a gp140 and a gp120.

In a particular embodiment, the boost composition comprises i) an MVA vector expressing membrane-bound HIV envelope protein associated with virus-like particles, ii) B.63521Δ11mutC receptor-binding subunit of gp120 and iii) the full-length single chain (FLSC) CD4-induced form of gp120.

B. Protein Boosts

The present invention provides compositions that comprise one or more HIV proteins that are used to boost a previously primed immune response. The full-length HIV envelope protein, gp160, is comprised of gp120 and gp41 subunits. HIV envelope glycoprotein gp120 is essential for virus entry into cells as it plays a vital role in attachment to specific cell surface receptors. While not to be bound by any particular mechanism, it is believed that reduced risk of HIV infection is associated with non-neutralizing antibodies to the V1V2, V3, C1 and conformational targets for the A32 monoclonal antibody regions of gp120.

In various embodiments, an MVA boost as described herein supplemented with a HIV peptide boost is contemplated.

In one embodiment, the one or more HIV proteins are HIV envelope (Env) proteins.

In one embodiment, the HIV Env protein is native or mutant HIV gp120.

In one embodiment, the HIV Env protein is the B.63521Δ11mutC receptor-binding subunit of gp120. The HIV peptide is gp120 (B.63521Δ11mutC) is a mutated gp120 from a transmitted, founder virus (Liao et al., J. Virol. 87:4185-4201, 2013). For B.63521Δ11mutC, the mutations include truncation of the 11 N-terminal amino acids to achieve better exposure of V1V2 (Alam et al., J Virol. 87:1554-1568, 2013) and mutation of a protease cleavage site in V3 to maintain integrity during production and storage (Yu et al., J. Virol. 84:1513-1526, 2010). Peptide B.63521Δ11mutC is the CD4-binding form of gp120.

In one embodiment, the HIV Env protein peptides comprise the full-length single chain (FLSC) form of gp120. The full length single chain (FLSC) is the CD4-induced form of HIV-1 BaL gp120 tethered to the D1D2 domains of CD4 by a 20-amino-acid linker (Fouts et al., J. Virol. 74:11427-11436, 2000; Vu et al., AIDS Research and Human Retroviruses, 22:477-490, 2006).

In one embodiment, the HIV Env protein is native or mutant HIV gp140.

In a particular embodiment, the boost composition comprises i) an MVA vector expressing membrane-bound HIV envelope protein associated with virus-like particles and ii) the B.63521Δ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
 a) B.63521Δ11mutC and FLSC,
 b) a gp120 and B.63521Δ11mutC,
 c) a gp120 and FLSC,
 d) a gp140 and B.63521Δ11mutC,
 e) a gp140 and FLSC, or
 f) a gp140 and a gp120.

In a particular embodiment, the boost composition comprises i) an MVA vector expressing membrane-bound HIV envelope protein associated with virus-like particles, ii) B.63521Δ11mutC receptor-binding subunit of gp120 and iii) the full-length single chain (FLSC) of gp120.

In this particular embodiment, the gp120 (B.63521Δ11mutC) boosts increase and broaden antibody responses to gp120 including the V1V2 and V3 loops of gp120 whereas the FLSC boosts increase and further broaden antibody responses to gp120 and the CD4-induced form of gp120 including the C1, V1/V2 and V3 regions of gp120 and conformational targets for the A32 monoclonal antibody.

In one embodiment, the boost composition may include 1, 2, 3, 4, 5 or more than 5 different gp120 peptides or variants thereof to boost a previously primed immune response to HIV.

Formulations

Pharmaceutically acceptable salts retain the desired biological activity of the parent peptide without toxic side effects. The term "pharmaceutically acceptable salt" as used herein refers to salts which are known to be non-toxic and are commonly used in the pharmaceutical literature. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenylsubstituted alkanoic acids, hydroxyalkanoic and hydroxyalkandioic acids, aromatic acids, aliphatic and aromatic sulfonic acids, may also be used. Such pharmaceutically acceptable salts include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, beta-hydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydrogenphosphate, dihydrogenphosphate, metaphosphate, pyrophosphate, propionate, phenylpropionate, salicylate, succinate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

Representative delivery regimens include oral, parenteral (including subcutaneous, intramuscular and intravenous injection), rectal, buccal (including sublingual), transdermal, inhalation ocular and intranasal. In one embodiment, delivery of compounds entails subcutaneous injection of a controlled-release injectable formulation. In some embodiments, compounds described herein are useful for subcutaneous, intranasal and inhalation administration.

The selection of the exact dose and composition and the most appropriate delivery regimen will be influenced by the pharmacological properties of the selected protein. Additionally, the route of administration will result in differential amounts of absorbed material. Bioavailabilities for administration of compounds through different routes are particularly variable, with amounts from less than 1% to near 100% being seen. Typically, bioavailability from routes other than intravenous, intraperitoneal or subcutaneous injection are 50% or less.

In accordance with the methods of the invention, a peptide as described herein, can be administered to a subject alone (e.g., as a purified peptide or compound), or as a component of a composition as described herein. The compositions can be formulated with a physiologically acceptable carrier or excipient to prepare a pharmaceutical composition. The carrier and composition can be sterile. The formulation should suit the mode of administration, for example intravenous or subcutaneous administration. Methods of formulating compositions are known in the art (see, e.g., Remington's Pharmaceuticals Sciences, 17th Edition, Mack Publishing Co., (Alfonso R. Gennaro, editor) (1989)).

Suitable pharmaceutically acceptable carriers include, but are not limited to, water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring and/or aromatic substances and the like) which do not deleteriously react with the active compounds or interference with their activity. In a preferred embodiment, a water-soluble carrier suitable for intravenous administration is used.

The composition, if desired, can also contain minor amounts of wetting or emulsifying agents, or pH buffering agents. The composition can be a liquid solution, suspension, emulsion, sustained release formulation, or powder. The composition can also be formulated as a suppository, with traditional binders and carriers such as triglycerides.

The composition can be formulated in accordance with the routine procedures as a pharmaceutical composition adapted for administration to human beings. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, the pharmaceutical composition comprise a liquid carrier such as, but not limited to, water, saline, phosphate buffered saline, Ringer's solution, dextrose solution, serum-containing solutions, Hank's solution, other aqueous physiologically balanced solutions, oils, esters and glycols.

The compounds as described herein can be formulated as neutral or salt forms. As stated above, pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The pharmaceutical formulations of the present invention may be administered by any route suitable for peptide immunization, including intradermal and intramuscular administration. Typically, the peptide is dissolved or suspended in a sterile injectable solution, at a concentration sufficient to provide the required dose in 0.5 to 2 ml or less.

Administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable materials can be sterilized for example, by filtration through a bacterial-retaining filter.

The pharmaceutical compositions may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Adjuvants

The term "adjuvant" as used herein refers to a compound that enhances a subject's immune response to an antigen when administered conjointly with that antigen.

Adjuvant-mediated enhancement of the immune response can be assessed by any method known in the art, including without limitation one or more of the following: (i) an increase in the magnitude of antibody to the antigen; (ii) a change in the characteristics of antibody to the antigen, such as isotype, or avidity, (iii) an increase in the number of CD4+ or CD8+ T cells recognizing the antigen; (iv) a change in the levels or types of cytokines being produced by white blood cells; and (v) an increase in in vivo protection after live challenge.

An immune response is believed to be enhanced, if any measurable parameter of antigen-specific immunoreactivity (e.g., antibody titer or T cell production) is increased at least 10% when a subject is challenged with an antigen and adjuvant compared to a subject challenged with the antigen alone. In certain embodiments of the present invention, an immune response is enhanced if any measurable parameter of antigen-specific immunoreactivity is increased by at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 95%, at least 100%, at least 125%, at least 150%, at least 175%, at least 200%, at least 225%, at least 250%, at least 275%, at least 300%, at least 350%, at least 400%, at least 450%, at least 500%, or at least 1000%.

Exemplary additional adjuvants include, but are not limited to, mineral gels such as aluminum hydroxide, aluminum salts (e.g., aluminum phosphate) or calcium salts (e.g., calcium phosphate); MF59, or SAF; adjuvant systems (AS01, AS02, AS03, ASO4) (GlaxoSmithKline), complete Freund's adjuvant, incomplete Freund's adjuvant, microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), lipopolysaccharides (LPS), mycobacteria, tetanus toxin, *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-1, IL-2, IL-12 or GM-CSF; synthetic adjuvants such as nonionic block copolymers or surfactants, muramyl peptide analogues (e.g., N-acetyl-muramyl-L-threonyl-D-isoglutamine [thr-MDP], N-acetyl-nor-muramyl-L-alanyl-D-isoglutamine, N-acetyl-muramyl-L-alanyl-D-isoglutaminyl-L-alanine-2-[1'-2'-dipalmitoyl-s-n-glycero-3-hydroxyphosphoryloxy]-ethylamine), polyphosphazenes, synthetic polynucleotides, surface active substances such as lysolecithin, pluronic polyols, polyanions, peptides, hydrocarbon emulsions, or keyhole limpet hemocyanins (KLH). Additional adjuvants include CMC (carboxyl methylcellulose), HPMC (hydroxypropyl methylcellulose), glucopyranosyl Lipid adjuvant (GLA), or polyICLC.

Other adjuvants are known to those of skill in the art and are contemplated for use with the vaccine and boost compositions described herein.

Kits

In some embodiments, the present invention further provides kits or other articles of manufacture which contain peptides such as B.63521Δ11mutC or FLSC and/or MVA vectors expressing HIV envelope proteins such as MVA expressing ADA gp140, pharmaceutical compositions described herein, as well as instructions for its reconstitution (if lyophilized) and/or use. Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyo-jects. The container may be formed from a variety of materials such as glass or plastic. In some embodiments, the container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may hold formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, the container may contain a single dose of a stable formulation containing peptide such as B.63521Δ11mutC or FLSC. In various embodiments, a single dose of the stable formulation is present in a volume of less than about 2.0 ml, about 1.5 ml, about 1.0 ml, or about 0.5 ml. Alternatively, the container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration for each protein in the reconstituted formulation will generally be at least about 300 µg/ml (e.g., at least about 50 µg/ml, at least about 100 µg/ml, at least about 200 µg/ml, at least about 400 µg/ml, at least about 500 µg/ml. In one embodiment, the protein concentration for a single protein-containing composition will be between about 50 µg/ml and 500 µg/ml, between about 100 µg/ml and 400 µg/ml, or between about 250 µg/ml and 350 µg/ml. This protein concentration will increase for each additional protein in the composition. Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

Dosage

When employed for therapeutic use, the compositions of the present invention are administered in the form of pharmaceutical compositions formulated for administration to a subject in pharmaceutically acceptable carriers. These pharmaceutically acceptable compositions represent further embodiments of the present invention.

For the priming compositions, one can arrive at an appropriate dosage when delivering DNA by way of a viral vector, just as one can when a plasmid vector is used. For example, one can deliver $1 \times 10^8$ pfu of an MVA-based vaccine, and administration can be carried out intramuscularly, intradermally, intravenously, subcutaneously or mucosally.

In one preferred regimen, DNA priming composition is administered at a dose of 250 µg up to 4 mg/injection, followed by MVA at a dose of $10^6$ to $10^9$ infectious virus particles/injection.

The compounds of the invention are useful in inducing or boosting an immune response to HIV and dosage amounts can be determined by routine methods of clinical testing to find the optimum dose.

In one embodiment, the protein dosage is between about 100 to 300 µg in an alum adjuvant. The alum adjuvant can be an aluminum phosphate or an aluminum hydroxide. Formulations can also be in other adjuvants, although alum is favored because protective immune responses were observed using this adjuvant in the partially effective RV144 trial.

IV. METHODS OF USE

The present invention relates to generation of an effective immune response to HIV. More specifically, methods are provided for eliciting both antibody and T cell (CD4+ and CD8+ T cell) responses and boosting antibody immune response without significant increase in CD4+ T cell response. More particularly, the present invention relates to "prime and boost" immunization regimens in which the immune response induced by administration of a priming composition is boosted by administration of a boosting composition. The present invention is based on the finding that effective boosting can be achieved using an MVA vector expressing an Env protein such as gp140 or a protein composition comprising one or more HIV proteins such as gp120 envelope proteins either with or without the simultaneous delivery of an MVA vector expressing VLPs. Priming can be accomplished with a variety of different types of priming compositions including a recombinant DNA vector, or a recombinant MVA vector.

The occurrence of differential stimulation of T cell responses is surprising because, for T cell responses, the gp120 protein, but not the MVA-gp140 boost, increased median CD4+ T cell responses (up to 5-fold). These increases were for IFNγ, IL2 and TNFα producing CD4+ T cells. Thus, both the gp120 protein boost and the MVA-expressed gp140 boost have the potential to augment protection of a DNA/MVA vaccine via increasing non-neutralizing antibody responses, while protection conferred by gp120 boost, but not MVA-gp140 boosts, may be decreased by increased CD4+ T cell responses.

Methods of supplemental boosting with a MVA expressing an Env subunit or protein are measured by assessing titer, isotype, specificity, breadth and function of antibody (Ab) to HIV Env. In a partially successful RV144 trial, reduced risk of HIV infection was associated with antibodies to the V1V2, V3, C1 and A32 regions of gp120 and ADCC activity of elicited antibodies. Methods of increasing protection against acquisition of HIV are measured in preclinical challenge studies in non-human primates using chimeras of human and simian immunodeficiency viruses (SHIVs) and in human efficacy trials.

In one aspect, the invention provides a method for inducing an immune response to HIV comprising:
1) administering a first composition to a subject in need thereof to prime an immune response to HIV;
2) administering a second composition comprising a) an MVA vector expressing membrane-bound HIV envelope protein associated with virus-like particles and b) one or more additional HIV proteins to boost the immune response.

In one embodiment, the MVA vector is MVA/HIV62B.

In one embodiment, the one or more HIV proteins are HIV envelope (Env) proteins.

In various embodiments, the one or more HIV Env proteins include, but are not limited to, native or mutant gp120 (for example B.6352lΔ11mutC, FLSC), native or mutant gp140 (for example ADA gp140), or MVA-expressed forms thereof.

In one embodiment, the HIV Env protein is native or mutant HIV gp120.

In one embodiment, the HIV Env protein is the B.6352lΔ11mutC receptor-binding subunit of gp120.

In one embodiment, the HIV Env protein peptides comprise the full-length single chain (FLSC) CD4-induced form of gp120.

In one embodiment, the HIV Env protein is native or mutant HIV gp140.

In a particular embodiment, the boost composition comprises i) an MVA vector expressing membrane-bound HIV envelope protein associated with virus-like particles and ii) the B.6352lΔ11mutC receptor-binding subunit of gp120.

In a particular embodiment, the boost composition comprises i) an MVA vector expressing membrane-bound HIV envelope protein associated with virus-like particles and ii) the FLSC CD4-induced form of Env.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
    a) B.6352lΔ11mutC and FLSC,
    b) a gp120 and B.6352lΔ11mutC,
    c) a gp120 and FLSC,
    d) a gp140 and B.6352lΔ11mutC,
    e) a gp140 and FLSC, or
    f) a gp140 and a gp120.

In a particular embodiment, the boost composition comprises i) an MVA vector expressing membrane-bound HIV envelope protein associated with virus-like particles, ii) B.6352lΔ11mutC receptor-binding subunit of gp120 and iii) the full-length single chain (FLSC) CD4-induced form of gp120.

In one embodiment, the one or more HIV proteins are expressed from an MVA vector.

In one embodiment, the boost composition comprises a first MVA vector expressing membrane-bound HIV envelope protein associated with virus-like particles, and one or more different MVA vectors expressing one or more secreted HIV Env proteins.

In one embodiment, the prime composition is administered about 8 weeks apart.

In one embodiment, the prime composition is administered at about week 0 and 8.

In one embodiment, the boost composition is administered about 8 weeks after the last priming composition administration.

In one embodiment, the boost composition is administered at least 2 times.

In one embodiment, the boost composition is administered about 3 times.

In one embodiment, the boost composition is administered at about week 16, 24 and 40 after administration of the first priming composition.

In one embodiment, the boost composition is administered at about week 8, 16 and 32 after the last priming composition.

One aspect of the present invention provides a method of boosting an antibody response to HIV Env in an individual, the method including provision in the individual of a composition comprising one or more HIV proteins, whereby an antibody response to the antigen previously primed in the individual is boosted.

It is possible that enhanced antibody responses decrease, or fail to enhance protection for DNA/MVA vaccines because protein boosts also enhance CD4+ T cell responses that are targets for infection and therefore undesirable. HIV vaccines have a history of potentially enhancing susceptibility to infection (Buchbinder, S. P *Lancet* 372, 1881-1893 (2008); Duerr, A., et al. *J Infect Dis* 206, 258-266 (2012)), a phenomenon that is thought to reflect immune activation enhancing CD4+ T cells targets for infection (Fauci, A. S., *Science* 344, 49-51 (2014)). As such, one of the advantages of the present methods is to boost protective antibody formation using MVA expressing HIV proteins. These MVA-expressed proteins enhance antibody responses but do not substantially enhance CD4+ T cell responses over those elicited by the MVA vector expressing VLPS. Thus supplementing the MVA-VLP boost with a MVA expressing an Env protein provides a protective advantage of enhanced antibody responses without the risk of increased CD4+ T cell targets for infection.

In one embodiment, an MVA vector expressing HIV antigens is administered before the second composition.

Another aspect of the invention provides a method of inducing a T cell immune response to an HIV antigen in an individual, and also eliciting an antibody response, the method comprising administering to the individual a priming composition comprising nucleic acid encoding the antigen and then administering a boosting composition comprising one or more HIV proteins.

In this aspect, the invention provides a method of inducing an immune response to HIV comprising:
    1) administering a first composition to a subject in need thereof to prime an immune response to HIV;
    2) administering a second composition comprising a) an MVA vector expressing HIV envelope protein associated with virus-like particles and b) one or more HIV proteins to boost the immune response.

In one embodiment, the MVA vector is MVA/HIV62B.

In one embodiment, the one or more HIV proteins are HIV envelope (Env) proteins.

In various embodiments, the one or more HIV Env proteins include, but are not limited to, native or mutant gp120 (for example B.6352lΔ11mutC, FLSC), native or mutant gp140 (for example ADA gp140), or MVA-expressed forms thereof.

In one embodiment, the HIV Env protein is native or mutant HIV gp120.

In one embodiment, the HIV Env protein is the B.6352lΔ11mutC receptor-binding subunit of gp120.

In one embodiment, the HIV Env protein peptides comprise the full-length single chain (FLSC) of CD4-induced gp120.

In one embodiment, the HIV Env protein is native or mutant HIV gp140.

In a particular embodiment, the boost composition comprises i) an MVA vector expressing membrane-bound HIV envelope protein associated with virus-like particles and ii) the B.6352lΔ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
    a) B.6352lΔ11mutC and FLSC,
    b) a gp120 and B.6352lΔ11mutC,
    c) a gp120 and FLSC,
    d) a gp140 and B.6352lΔ11mutC,
    e) a gp140 and FLSC, or
    f) a gp140 and a gp120.

In a particular embodiment, the boost composition comprises i) an MVA vector expressing membrane-bound HIV envelope protein associated with virus-like particles, ii) B.6352lΔ11mutC receptor-binding subunit of gp120 and iii) the full-length single chain (FLSC) CD4-induced form of gp120.

In one embodiment, the one or more HIV proteins are expressed from an MVA vector.

In one embodiment, the boost composition comprises a first MVA vector expressing membrane-bound HIV envelope protein associated with virus-like particles, and one or more different MVA vectors expressing one or more secreted HIV Env proteins.

In one embodiment, the prime composition is administered about 8 weeks apart.

In one embodiment, the prime composition is administered at about week 0 and 8.

In one embodiment, the boost composition is administered about 8 weeks after the last priming composition administration.

In one embodiment, the boost composition is administered at least 2 times.

In one embodiment, the boost composition is administered about 3 times.

In one embodiment, the boost composition is administered at about week 16, 24 and 40 after administration of the first priming composition.

In one embodiment, the boost composition is administered at about week 8, 16 and 32 after the last priming composition.

In another aspect, the invention provides a method of priming and boosting an immune response to HIV comprising:

administering a composition to a subject in an effective amount to induce and boost an immune response to HIV wherein the composition comprises: i) a first MVA vector expressing membrane-bound HIV envelope protein associated with virus-like particles, and ii) at least one HIV protein.

In one embodiment, the MVA vector is MVA/HIV62B.

In one embodiment, the one or more HIV proteins are HIV envelope (Env) proteins.

In various embodiments, the one or more HIV Env proteins include, but are not limited to, native or mutant gp120 (for example B.6352lΔ11mutC, FLSC), native or mutant gp140 (for example ADA gp140), or MVA-expressed forms thereof.

In one embodiment, the HIV Env protein is native or mutant HIV gp120.

In one embodiment, the HIV Env protein is the B.6352lΔ11mutC receptor-binding subunit of gp120.

In one embodiment, the HIV Env protein peptides comprise the full-length single chain (FLSC) CD4-induced form of gp120.

In one embodiment, the HIV Env protein is native or mutant HIV gp140.

In a particular embodiment, the boost composition comprises i) an MVA vector expressing membrane-bound HIV envelope protein associated with virus-like particles and ii) the B.6352lΔ11mutC receptor-binding subunit of gp120.

In a particular embodiment, the boost composition comprises i) an MVA vector expressing membrane-bound HIV envelope protein associated with virus-like particles and ii) the FLSC CD4-induced form of gp120.

In a particular embodiment, the boost composition comprises i) an MVA vector expressing membrane-bound HIV envelope protein associated with virus-like particles and ii) gp140.

In particular embodiments, the boost composition comprises i) an MVA vector expressing membrane-bound HIV envelope protein associated with virus-like particles and ii) two HIV envelope (Env) proteins selected from:
a) B.6352lΔ11mutC and FLSC,
b) a gp120 and B.6352lΔ11mutC,
c) a gp120 and FLSC,
d) a gp140 and B.6352lΔ11mutC,
e) a gp140 and FLSC, or
f) a gp140 and a gp120.

In a particular embodiment, the boost composition comprises i) an MVA vector expressing membrane-bound HIV envelope protein associated with virus-like particles, ii) B.6352lΔ11mutC receptor-binding subunit of gp120 and iii) the full-length single chain (FLSC) CD4-induced form of gp120.

In one embodiment, the one or more HIV proteins are expressed from an MVA vector.

In one embodiment, the boost composition comprises a first MVA vector expressing membrane-bound HIV envelope protein associated with virus-like particles, and one or more different MVA vectors expressing one or more HIV Env proteins.

In one embodiment, the prime composition is administered about 8 weeks apart.

In one embodiment, the prime composition is administered at about week 0 and 8.

In one embodiment, the boost composition is administered about 8 weeks after the last priming composition administration.

In one embodiment, the boost composition is administered at least 2 times.

In one embodiment, the boost composition is administered about 3 times.

In one embodiment, the boost composition is administered at about week 16, 24 and 40 after administration of the first priming composition.

In one embodiment, the boost composition is administered at about week 8, 16 and 32 after the last priming composition.

Another aspect provides for use of a protein composition, as disclosed herein, in the manufacture of a medicament for administration to a subject to boost an immune response to an HIV antigen, including an antibody response. Such a medicament is generally for administration following prior administration of a priming composition comprising DNA vector or MVA vector encoding HIV VLPs.

In particular embodiments of the various aspects of the present invention, administration of a priming composition is followed by boosting with a boosting composition, or first and second boosting compositions, the first and second boosting compositions being the same or different from one another. Still further boosting compositions may be employed without departing from the present invention.

In one embodiment, a triple immunization regime employs DNA, then MVA as a first boosting composition, then protein composition as a second boosting composition, optionally followed by a further (third) boosting composition or subsequent boosting administration of one or other or both of the same or different vectors.

In another embodiment, a triple immunization regime employs DNA, then MVA as a first boosting composition, then MVA as a second boosting composition, optionally followed by a further (third) boosting composition or subsequent boosting administration of protein composition.

Routes of Administration

A peptide composition as described herein (or a composition containing the peptide compositions as described herein) may be administered by any appropriate route. In some embodiments, the peptide composition is administered parenterally. In some embodiments, the parenteral administration is selected from intravenous, intradermal, inhalation, transdermal (topical), intraocular, intramuscular, subcutaneous, intramuscular, and/or transmucosal administration. In some embodiments, a peptide composition agent as described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, a peptide composition as described herein is administered intravenously. Alternatively, a peptide composition as described herein (or a composition containing a peptide composition as described herein) can be administered by inhalation, parenterally, intramuscularly, subcutaneously, intradermally, transdermally, or transmucosally (e.g., orally or nasally). More than one route can be used concurrently, if desired.

Dosing Schedules

Various embodiments may include differing dosing regimens.

In various embodiments, the vectors and protein compositions described herein are administered at intervals of 3 weeks, 4 week, 5 week, 6 weeks, 7 weeks, 8 weeks, 9 weeks, 10 weeks, 11 weeks, 12 weeks, and greater than 12 weeks.

In one embodiment, the boost composition is administered at about 8 weeks apart.

In various embodiments, the vectors and protein compositions described herein are administered at least 2 times, at least 3 times, at least 4 times, at least 5 times, at least 6 times at least 7 times, at least 8 times, at least 9 times, or at least 10 times.

In various embodiments, the vectors and protein compositions described herein are administered between 2 and 6 times, between 2 and 5 times, between 2 and 4 times, between 3 and 6 times, between 3 and 5 times.

In one embodiment, the composition is administered about 3 times.

The DNA and MVA vectors express HIV antigens. Exemplary vectors are DNA plasmid pGA2/JS7 or pGA2/JS7.1 (D). In one embodiment, one such MVA vector expressing HIV antigens is MVA/HIV62B (M).

In one embodiment, DNA vector is administered once and then again after 8 weeks (DD) to prime an immune response. MVA and protein (P) composition are administered at weeks 16, 24 and 40 after initial DNA prime (M+P, M+P, M+P).

In one embodiment, DNA vector is administered once and then again after 8 weeks (DD) to prime an immune response. Protein composition is administered to boost the primed immune response at about weeks 16, 24 and 40 after initial DNA prime (PPP).

In one embodiment, DNA vector is administered once and then again after 8 weeks (DD) to prime an immune response. MVA and protein composition are administered to boost the primed immune response at about weeks 16, 24 and 40 after initial DNA prime (M+P, M+P, M+P). Protein composition is administered at weeks 48 and 56 (PP).

In one embodiment, DNA vector is administered once and then again after about 8 weeks (DD) to prime an immune response. MVA-antigens and MVA-gp140 (M140) composition are administered to boost the primed immune response at about weeks 16, 24 and 40 after initial DNA prime (M+M140, M+M140, M+M140).

In one embodiment, MVA vector is administered once and then again after about 8 and 16 weeks (MMM). MVA and protein composition is administered at about weeks 24 and 32 and 48 after initial MVA prime (M+P, M+P, M+P).

In one embodiment, MVA vector is administered once and then again after about 8 and 16 weeks (MMM). MVA and protein composition are administered at about weeks 16, 24 and 40 after initial MVA prime (M+P, M+P, M+P). Protein composition is administered later at weeks 56 and 108 (PP).

In one embodiment, MVA vector is administered once and then again after about 8 and 16 weeks (MMM). MVA and MVA-expressing gp140 composition are administered at about weeks 16, 24 and 40 after initial MVA prime (M+M140, M+M140, M+M140). Protein composition is administered later at weeks 56 and 108 (PP).

All publications and patent applications mentioned in this specification are herein incorporated by reference to the same extent as if each independent publication or patent application is specifically and individually indicated to be incorporated by reference.

EXAMPLES

Example 1: GV-M1—Boosting an Immune Response to HIV Using a Monovalent B.63521Δ11mutC gp120 Protein or an MVA-Expressing Secreted gp140 with the GOVX-B11 DNA/MVA Vaccine GOVX-B11 is a combination DNA/MVA vaccine that expresses virus-like particles (VLPs) displaying trimeric membrane bound Env. It has demonstrated unique properties and shown considerable promise in both preclinical and clinical studies. The HIV Vaccine Trials Network (HVTN), an international collaboration, supported by the U.S. National Institutes of Health (NIH), has completed three Phase 1 trials (HVTN 045, HVTN 065, and HVTN 094) and a 300 subject Phase 2a trial (HVTN 205) and is currently preparing to conduct HVTN 114.

Summary

Protein boosts of DNA or live-vectored primes enhance antibody responses elicited by candidate human immunodeficiency virus vaccines. Antibody responses were enhanced to the human immunodeficiency virus envelope protein (Env) by supplementing the modified vaccinia Ankara (MVA) boosts in a DNA/MVA regimen with either an alum-adjuvanted gp120 Env subunit protein or a second MVA expressing a secreted gp140 ectodomain of Env (MVA-gp140). Five rhesus macaques per group were vaccinated with 2 primes at weeks 0 and 8 followed by three boosts at weeks 18, 26 and 40. Post the $3^{rd}$ boost, both supplements increased median antibody responses to a panel of 8 reference gp120 subunits by ~4-fold, and a panel of 16 reference V1V2 proteins by ~2-fold.

However, the two supplements differed in temporal responses: the gp120-boosted responses had higher magnitude and breadth of antibody responses post the $2^{nd}$ boost whereas the MVA-gp140 boosted antibody responses were both more durable and more boostable and were similar in height to the gp120-boosted responses after the $3^{rd}$ boost. Antibody responses to the V3 linear epitope dominated for all groups, with these being particularly enhanced by the gp120 supplement whereas the MVA-gp140 supplement brought out antibody responses to linear C5 and C2.2 envelope epitopes. Neutralizing antibody responses for the gp120 group were transiently higher after the $2^{nd}$ boost for Tier 1 and Tier 2 viruses (p<0.05 for MW965 [Tier 1C] and 25710 [Tier 2C]), but comparably enhanced for both supplemented groups after the $3^{rd}$ boost. Both boosts enhanced antibody-dependent cellular cytotoxicity (ADCC) for bound gp120.

As for T cell responses, the gp120, but not the MVA-gp140 boost, increased median CD4+ T cell responses (up to 5-fold). These increases were for IFNγ, IL2 and TNFα producing CD4+ T cells. Thus, both the gp120 protein boost and the MVA-expressed gp140 boost have the potential to augment protection of a DNA/MVA vaccine via increasing non-neutralizing antibody responses, while protection conferred by the gp120 boost, but not the MVA-gp140 boosts, may be decreased by increased CD4+ T cell responses.

Materials and Methods

Immunogens. The GOVX-B11 vaccine includes the pGA2/JS7 DNA and MVA/HIV62B (MVA62B) immunogens. The DNA prime expresses VLPs displaying the ADA gp160 Env. The DNA used in this trial also co-expressed rhesus GM-CSF (c; Hellerstein, M. 2012, Hum Vaccin Immunother 8). The DNA was produced, purified and resuspended in a proprietary buffer at 3 mg/ml at Aldevron (Fargo N. Dak.). MVA/HIV62B (MVA62B) expresses VLPs displaying ADA gp150 Env (Wyatt. L. et al., 2004, AIDS Res Hum Retroviruses 20:645-653; Wyatt, L. et al. 2008, Vaccine 26:486-493).

MVA62B (lot 001-03-12) was produced in CEF at IDT Biologica, purified by tangential flow filtration, and resuspended at $1 \times 10^8$ TCID50 per ml in a proprietary buffer for storage and inoculation. MVA-gp140 encodes a secreted ADA gp140 Env that was inserted into deletion II of MVA by plasmid insertion vector pLAS-2 and contained the same HXB2/BH10 gag pol as MVA 62B. MVA-gp140 was produced in CEF at the Laboratory for Viral Diseases, NIAID, NIH; purified by sucrose pad centrifugation and resuspended at 1×108 TCID50 per ml in a proprietary buffer for storage and inoculation. B63521Δ11 was produced by transient transfection at the Duke Human Vaccine Institute, Duke University. In order to prevent proteolytic clipping, mutations were introduced into the B63521Δ11 gp120 V3 (SIR-GPGQT) region. Antigenicity analysis with a panel of monoclonal antibodies (mAb) showed similar affinities of binding of sCD4, CD4 binding site bnAbs (VRC01, CH103), and glycan V3 bnAbs (PGT128, PGT125, PGT121), as well the V3 loop mAb 19b.

Study Design. The animal study was conducted at Bioqual Inc, Rockville Md. in accordance with all rules of the American Association for Laboratory Animal care and under the supervision of the Institutional Animal Clinical Care and Use Committee. Three-year-old male rhesus macaques, pre-screened for background for Env binding Ab and activated T cells, were randomized into 3 study groups of 5 animals each by weight. For all groups, 3 mg of DNA was inoculated by needle and syringe into the upper left limb on weeks 0 and 8 and 1×108 TCID50 of MVA/HIV-62B into the upper left limb on weeks 18, 26 and 40. At the time of the MVA boosts, animals in group 2 also received 100 µg of B63521Δ11mutC gp120 plus 500 µg of Alhydrogel (Brenntag Biosector, CAS 21645-51-2) and animals in group 3 also received $1 \times 10^8$ TCID50 of MVA-gp140, both delivered intramuscularly in 1 ml by needle and syringe to the upper right limb. Sera, PBMC, and rectal swabs were collected at regular intervals throughout the trial. Lymph nodes as well as an exsanguination bleed were collected at the end of the trial, 2 weeks following the last boost. The general health, weights, clinical blood counts (CBC) and clinical chemistries of animals were monitored throughout the trial.

Assays for Antibodies. Binding antibodies were tested both in Enzyme-linked-immunosorbent-assays (ELISA) and in Binding antibody multiplex assays (BAMA). The ELISAs uses con6-gp120 produced in BHK cells (Duke) and gp41 produced in bacteria (NIH AIDS Reagent Program, cat #12027) as antigens for antibodies to gp120 and gp41 respectively. Assays were done using a standard curve of macaque IgG captured by goat anti-rhesus antibody and results interpolated to estimate µg of specific antibodies per ml as previously described (Vaccine 26:486-493). BAMA were conducted as previously described (Zolla-Pazner, S. 2014 PLoS One 9:e87572; Yates, N L, 2014, Sci Transl Med 6:228ra239; Tomaras, G D, 2014, Vaccines (Basel) 2:15-35). Antibody titers (area under the curve, AUC) are determined by serial dilutions of rhesus plasma (1:400, 5-fold) for the following antigens (provided by Drs. Liao/Haynes, Duke University unless otherwise indicated): Gp41 (Subtype B) Immunodiagnostics; Group M consensus (ConSgp140CFI and Con6gp120/B); and B.63521_D11gp120MutC (vaccine strain). The breadth of IgG response was characterized using a down-selected antigen panel developed by the Antigen Reagent Program (ARP) (funded by CAVD-CAVIMC) for consistently measuring bAb breadth in AIDS clinical trials (manuscript in preparation). This panel consists of well-characterized HIV-1 envelope glycoprotein antigens as gp120 and oligomeric gp140 proteins (provided by Drs. Liao/Haynes, Duke University unless otherwise indicated), and gp70-V1/V2 scaffolds (provided by Dr. Pinter, State University of New Jersey). Plasma samples were tested at dilution 1:80 and 1:400 for binding breadth BAMA. MFI values within the linear range of the assay were used in breadth analysis. All assays are run under cGLP compliant conditions, including tracking of positive controls by Levy-Jennings charts using 21CFR Part 11 compliant software. Positive controls included HIVIG and CH58 mAb titrations. Negative controls included in every assay were blank beads, HIV-1 negative sera, and baseline (pre-vaccination) samples. To control for antigen performance, we used the preset criteria that the positive control titer (HIVIG) included on each assay (and for assays with V1V2 antigens, CH58 mAb) had to be within +/−3 standard deviations of the mean for each antigen (tracked with a Levy-Jennings plot with preset acceptance of titer (calculated with a four-parameter logistic equation, SigmaPlot, Systat Software).

Linear epitope mapping. Serum epitope mapping of heterologous strains was performed as previously described (Shen, X. et al, 2015, J Virol 89:8643-8650; Tomaras, G D, et a., 2011, *J Virol* 85:11502-11519; Gotardo, R. et al., 2013, *PLoS One* 8:e75665) with minor modifications. Briefly, array slides were provided by JPT Peptide Technologies GmbH (Germany) by printing a library designed by Dr. B. Korber, Los Alamos National Laboratory, onto Epoxy glass slides (PolyAn GmbH, Germany). The library contains overlapping peptides (15-mers overlapping by 12) covering 6 full length gp160 consensus sequences (Clade A, B, C, D, Group M, CRF1, and CRF2), and gp120 sequences of 6 vaccine strains (MN, A244, Th023, TV-1, ZM641, 1086C). 3 identical subarrays, each containing the full peptide library, were printed on each slide. All array slides were blocked for 1 hour, followed by a 2 hr incubation with 1:50 diluted test sera and a subsequent 45 min incubation with Goat Anti-Hu IgG conjugated with AF647 (Jackson ImmunoResearch, PA). Array slides were scanned at a wavelength of 635 nm with an InnoScan 710 AL scanner (Innopsys, Carbonne, FRANCE) using XDR mode. Images were analyzed using MagPix 8.0 software to obtain binding intensity values for all peptides. Binding of postimmunization serum to each peptide was subtracted of its own baseline value, which was defined as the median signal intensity of the triplicates of the peptide for the matched prebleed serum plus 3 times the standard error of the triplicates. Binding magnitude to each identified epitope was defined as the highest binding by a single peptide within the epitope region.

Avidity. The affinity maturation of the vaccine-elicited antibody responses to the immunodominant region of gp41 (Bcon03 ID epitope tetramer) was measured by an avidity index assay using the binding antibody multiplex assay (BAMA), Avidity index was measured by inclusion of a denaturation step (treating the samples with 0.1 M Na-citrate, pH3.0) and comparing the MFI in the treated well vs. MFI in the untreated well (Wei, X., et al. 2010, AIDS Res Hum Retroviruses 26:61-71). Untreated wells contain Phosphate Buffered Saline (PBS) during the avidity incubation step. Avidity index (AI) is defined as 100*MFI in the treated divided by MFI in the untreated well.

ADCC-GranToxiLux (ADCC-GTL) Assay. Antibody dependent cellular cytotoxic activity mediated by the participants' plasma/sera was detected according to a modification of the previously described GranToxiLux (GTL) cell-mediated cytotoxicity procedurePollara, J. et al., 2011, Cytometry A 79:603-612). The CEM.NKRCCR5 target cells were coated with recombinant gp120 HIV-1 protein derived from Env of HIV-1 BaL (Genebank No. M68893; provided by Dr. Liao-Duke Human Vaccine Institute), ADA (Genebank No. M60472; MyBioSource), and Con6 (provided by Dr. Liao-Duke Human Vaccine Institute). The assay readout is the percent of antigen coated target cells taking up Granzyme B. A positive response is defined if the peak percent Granzyme B activity across six dilutions is greater than or equal to 8%.

Neutralizing antibodies. Neutralizing antibodies were measured as a function of reductions in luciferase (Luc) reporter gene expression after a single round of infection in TZM-bl cells (Montefiori, D C, 2009, Methods Mol Biol 485:395-405; Sarzotti-Kelsoe M. et al., 2014, J Immunol Methods 409:16). TZM-bl cells (also called JC57BL-13) were obtained from the NIH AIDS Research and Reference Reagent Program, as contributed by John Kappes and Xiaoyun Wu. Briefly, a pre-titrated dose of virus was incubated with serial 3-fold dilutions of test sample in duplicate in a total volume of 150 µl for 1 hr at 37° C. in 96-well flat-bottom culture plates. Freshly trypsinized cells (10,000 cells in 100 µl of growth medium containing 75 µg/ml DEAE dextran) were added to each well. One set of 8 control wells received cells+virus (virus control) and another set received cells only (background control). After 48 hours of incubation, 100 µl of cells was transferred to a 96-well black solid plate (Costar) for measurements of luminescence using the Britelite Luminescence Reporter Gene Assay System (PerkinElmer Life Sciences). Assay stocks of molecularly cloned Env-pseudotyped viruses were prepared by transfection in 293T/17 cells (American Type Culture Collection) and titrated in TZM-bl cells as described (Montefiori, D C, 2009, Methods Mol Biol 485:395-405). This assay has been formally optimized and validated (Sarzotti-Kelsoe M. et al., 2014, J Immunol Methods 409:16) and was performed in compliance with Good Clinical Laboratory Practices, including participation in a formal proficiency testing program.

T cell responses. HIV-specific cellular immune responses were assessed by multiparameter intracellular cytokine staining (ICS) assays following stimulation with HIV peptides (15 mers overlapping by 11) as previously described (Kwa, S. et al, 2015, J Virol 89:4690-4695). Panel one used anti-IFN-γ (clone B27), anti-IL-2 (clone MQ1-17H12), and anti-TNF-α (clone MAb11) antibodies, and a 2nd panel used anti-CD40L (clone TRAP1), anti-IL-4 (clone 8D4-8) and anti-IL-21 (clone 3A3-N2.1) antibodies. Both panels sorted cells using anti-CD3 (clone SP34-2), anti-CD4 (clone L200), and anti-CD8 (clone SK1) antibodies. All antibodies were obtained from BD Biosciences. Both panels also sorted live cells using Live/Dead Fixable Green Stain Kit (ThermoFisher Scientific).

Statistics.

Antibody and T cell response measurements were first screened in an omnibus test. Differences between pairs of groups in the levels of measurements that showed a p value of <0.05 were further tested using Wilcoxon rank sum exact test. Statistical significance indicated on figures are based on p values that are not controlled for multiple comparison (raw_p).

Results

Figure 1B:
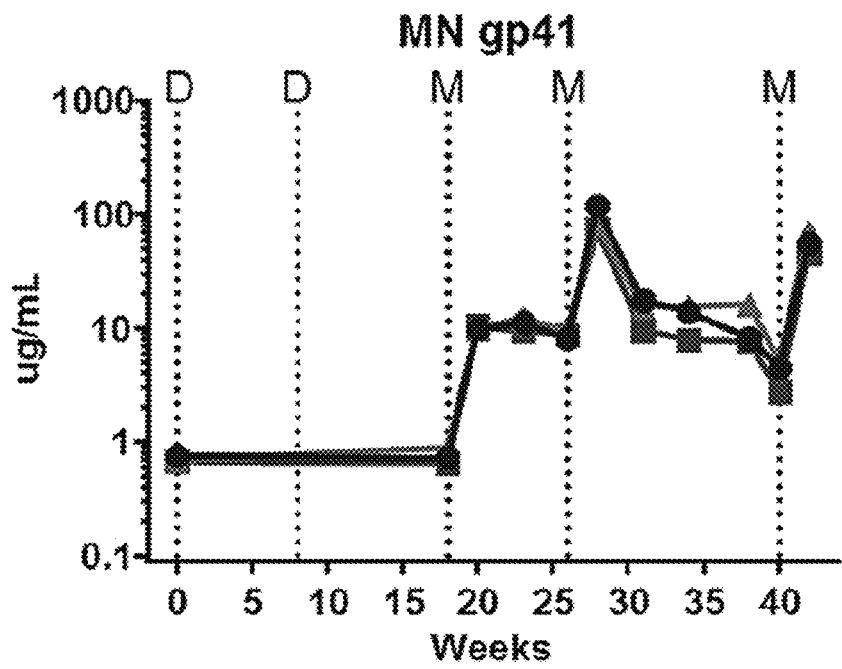

Serum binding antibody response. Binding antibody responses against a consensus group M gp120 (Con6) and MN gp41 recombinant proteins were measured using ELISAs and longitudinal serum samples. Gp120 and gp41-specific IgG responses developed after the first MVA boost (week 18), peaked after the second boost (week 28) declined with time and were boosted again with the $3^{rd}$ boost (FIG. 1A and FIG. 1B). At 2 weeks after the $2^{nd}$ boost (week 28), the MVA+gp120 group elicited the highest levels of Con6 gp120-specific binding with a median titer about 10-fold higher than that of the MVA-only group and 2.5-fold higher than that of the MVA+MVA-gp140 group (FIG. 1A). At this time, the median titer of the MVA+MVA-gp140 boosted group was 3 times higher than that of the non-supplemented group. Following the $3^{rd}$ MVA boost, the MVA+gp120 and MVA+MVA-gp140 groups had similar median magnitudes of Ab whereas the titer elicited by MVA-only was 4-fold lower. However, the differences among groups were not significant (FIGS. 1A&1B). Binding magnitudes for MN gp41 were overall comparable among groups at all time points tested (FIG. 1B).

Binding to the B63521Δ11mutC gp120 protein used for boosting was measured in BAMA. For this matched antigen, The MVA+gp120 group showed significantly higher responses following the $2^{nd}$ MVA boost, post contraction at the time of the $3^{rd}$ boost and after the $3^{rd}$ boost compared to both the MVA-only and MVA+MVA-gp140 group. The differences between the MVA+gp120 group and the MVA+MVA-gp140 group were 13.8-fold at wk 28 and 5.2-fold at wk42.

Figure 1C:
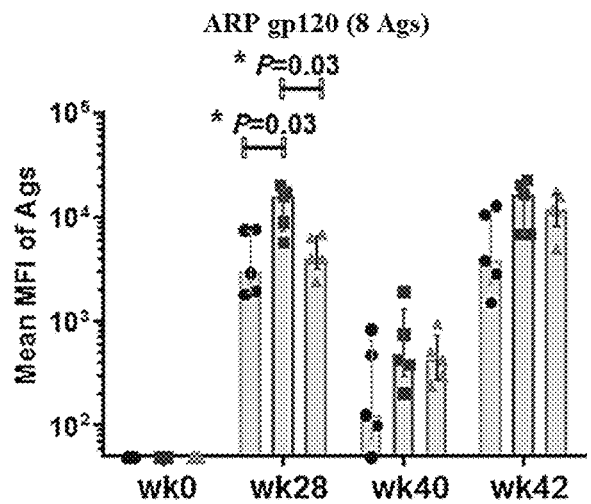
Figure 1D:
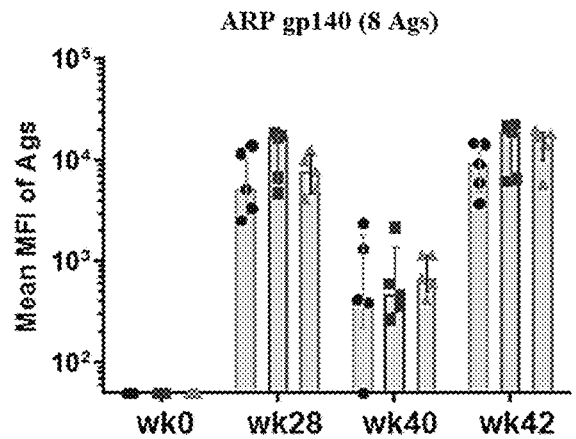
Figure 1E:
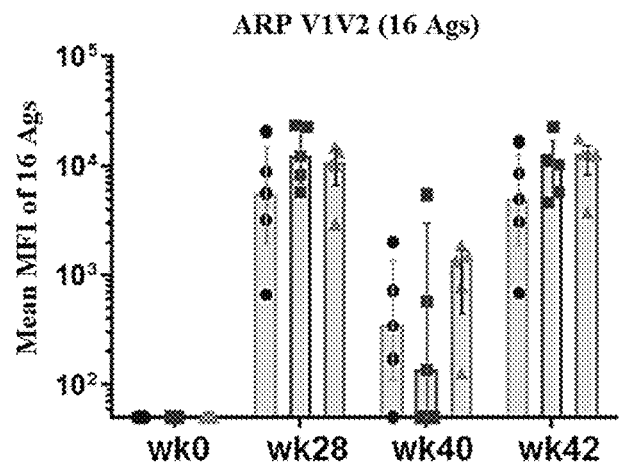
Figure 1F:
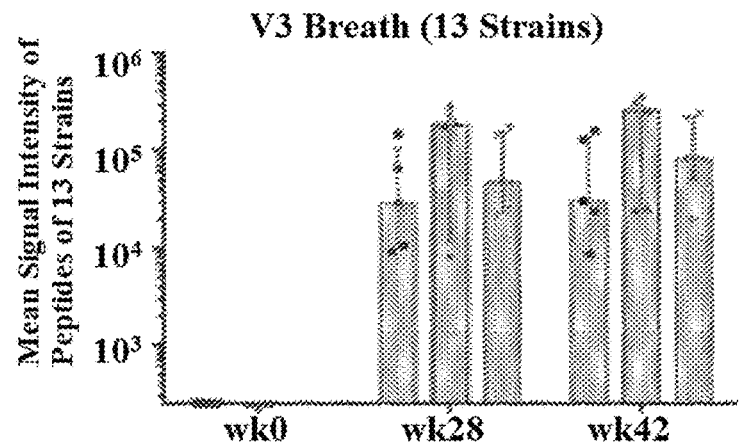

Breadth of binding antibody response. Following the $3^{rd}$ boost, the two supplemented groups had similar magnitudes of antibody responses for gp120 and V1V2 (FIG. 1, Table 5). The breadth of binding Ab was evaluated using Env and V1V2 breadth panels down-selected by the Gates Foundation Collaboration for AIDS Vaccine Discovery. At 2 weeks post the $2^{nd}$ boost (wk28), the mean binding magnitude (MFI) for the panel of 8 gp120 antigens was higher for the MVA+gp120 group (15,914) compared to the MVA+MVA-gp140 group (4,060) and the MVA-only group (2,963) (raw p=0.03 for each) (FIG. 1C, Table. 5). Group median binding magnitudes to the panel of 8 gp140 antigens was also highest post the $2^{nd}$ boost for the MVA+gp120 group (FIG. 1D), with group medians of 16,799, compared to 7,794 and 5,215 for MVA+MVA-gp140 and MVA-only groups, respectively (Table 5); however, these differences were not statistically significant. Binding to the V1V2 panel was similar for sera from the MVA+gp120 and MVA+MVA-gp140 groups and about 2-fold higher than for the non-supplemented immunizations after both the $2^{nd}$ and $3^{rd}$ boosts (Table 5). Magnitude/breadth of binding to 13 V3 linear peptides trended higher for the MVA+gp120 group compared to the other 2 groups after both the $2^{nd}$ and $3^{rd}$ boosts by 3- to 8-fold for group median V3 signal intensities (FIG. 1F; Table 5).

TABLE 5

Group median magnitude for binding to each antigen panels in FIG. 1C-1F, the fold increase over MVA-only group, and the fold of contraction and boost

| Antigen Panel | Group | Binding Magnitude | | | Fold over MVA-only group | | | Contraction | Boost |
|---|---|---|---|---|---|---|---|---|---|
| | | wk 28 | wk 40 | wk 42 | wk 28 | wk 40 | wk 42 | wk 28/wk 40 | wk 42/wk 28 |
| ARP gp120 (8 Ags) | MVA only | 2,963 | 127 | 3,895 | — | — | — | 15.7 | 1.4 |
| | +GP120 | 15,914 | 427 | 16,660 | 5.4 | 3.4 | 4.3 | 13.7 | 1.1 |
| | +MVAgp140 | 4,060 | 427 | 11,855 | 1.4 | 3.4 | 3.0 | 8.1 | 2.6 |
| ARP gp140 (8 Ags) | MVA only | 5,215 | 424 | 9,223 | — | — | — | 8.7 | 1.5 |
| | +GP120 | 16,799 | 466 | 19,009 | 3.2 | 1.1 | 2.1 | 17.7 | 1.2 |
| | +MVAgp140 | 7,794 | 680 | 17,323 | 1.5 | 1.6 | 1.9 | 8.8 | 1.8 |
| ARP V1V2 (16 Ags) | MVA only | 5,670 | 350 | 5,026 | — | — | — | 13.3 | 1.0 |
| | +GP120 | 12,308 | 136 | 10,477 | 2.2 | 0.4 | 2.1 | 42.6 | 0.9 |
| | +MVAgp140 | 10,808 | 1,347 | 12,685 | 1.9 | 3.8 | 2.5 | 8.0 | 1.2 |
| V3 (13 strains) | MVA only | 28,871 | nd | 30,425 | — | — | — | na | 1.1 |
| | +GP120 | 180,262 | nd | 255,836 | 6.2 | na | 8.4 | na | 1.8 |
| | +MVAgp140 | 46,549 | nd | 81,135 | 1.6 | na | 2.6 | na | 1.2 |

Figure 2A:
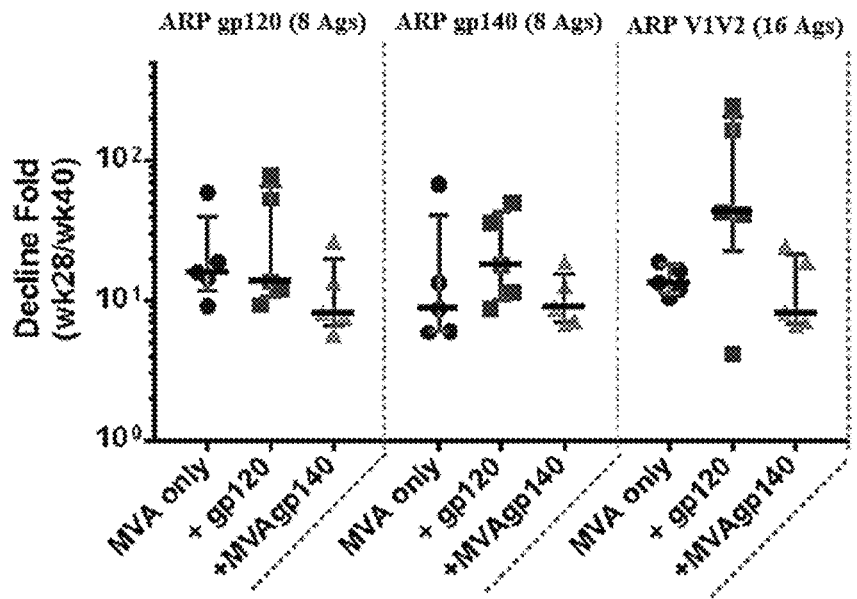
Figure 2B:
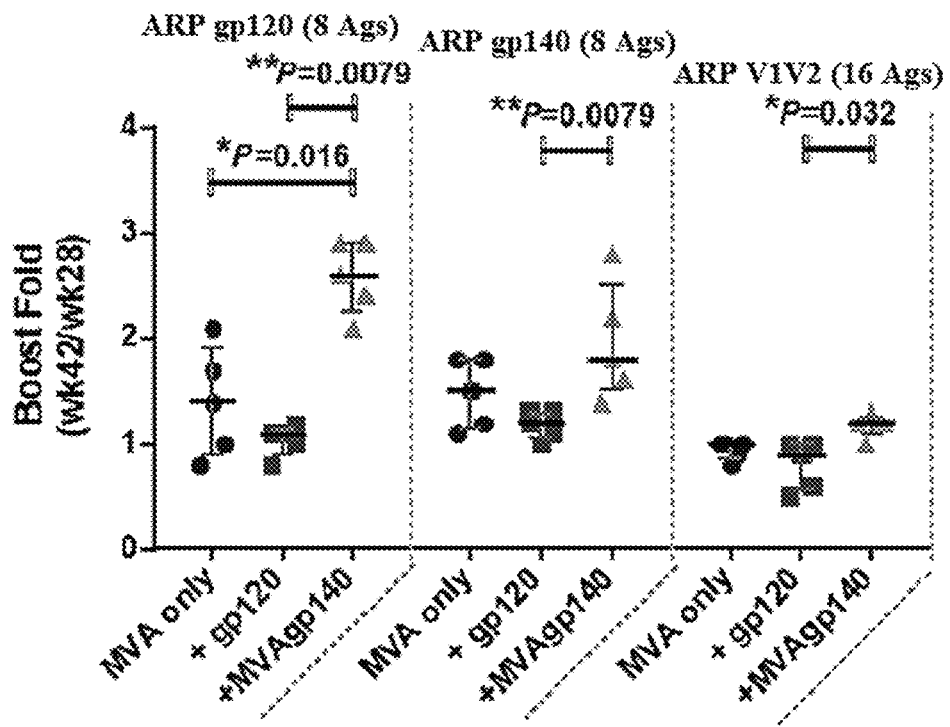

The durability and ability to boost binding antibody responses were evaluated as the fold decline of the Ab response over the 12 weeks following the 2$^{nd}$ boost (week 28/week 40) and the fold increase of the Ab response following the 3$^{rd}$ boost over that following the 2$^{nd}$ boost (week 42/week 40) (FIG. 2). The MVA+gp120 boosted group underwent the largest declines (FIG. 2A, Table 5). For this group, the median fold declines were 13.7 (9.1-59.3), 17.7 (8.6-49.2) and 42.6 (4.1-246.2) for the gp120, gp140 and V1V2 antigen panels respectively as compared to 8.1 (5.7-26.1), 8.8 (6.7-18.6) and 8.0 (6.6-23.8) for the MVA+MVA-gp140 group (Table 5). However, the differences were not significant among groups. By the 3$^{rd}$ boost, the MVA+gp120 group also showed the weakest boost for all 3 antigen panels (FIG. 2B). Median boosting ratios for the MVA+MVA-gp140 and MVA+gp120 groups were 2.6 (2.1-2.9) versus 1.1 (0.8-1.2) for the gp120 panel, 1.8 (1.4-2.8) versus 1.2 (1.0-1.3) for the gp140 panel, and 1.2 (1.0-1.3) versus 0.9 (0.5-1.0) for the V1V2 panel respectively.

Figure 3A:
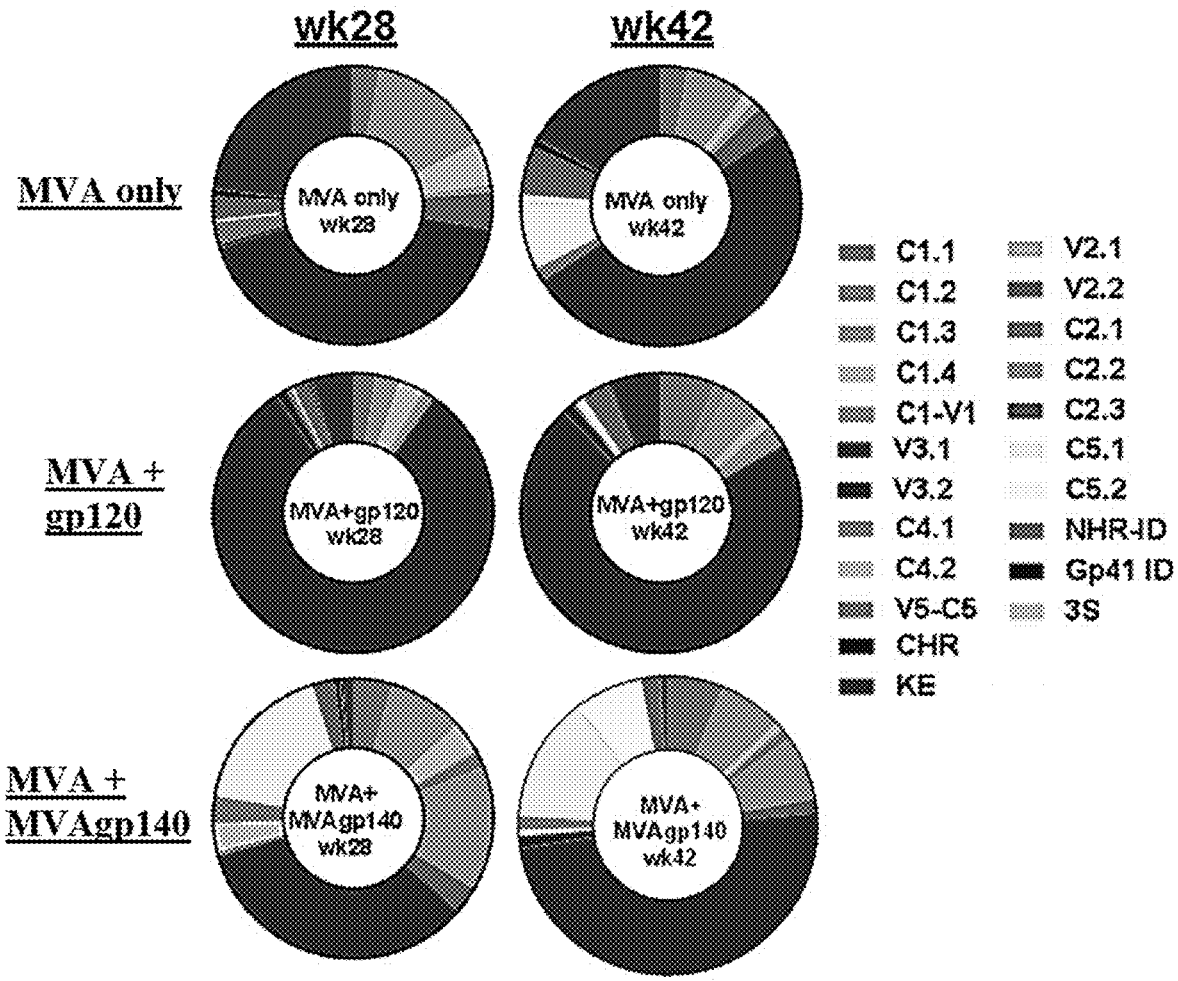

Specificity for linear peptides of binding antibodies. Specificities of elicited IgG were tested following the 2$^{nd}$ and 3$^{rd}$ boosts for recognition of linear epitopes across overlapping Env peptides representing consensus sequences from major clades and circulating recombinant forms as well as gp120s from vaccine strains. Plasma IgG from the vaccinated animals targeted linear epitopes in the C1, V2, C2, V3, C4, and C5 regions of gp120. In gp41 it targeted a peptide spanning the C-terminus of the N-heptad repeat and the N-terminus of the gp41 immunodominant region (NHR_ID), the gp41 immunodominant region (gp41_ID), 3S (an epitope C-terminal to the gp41_1D that contains 3 serine residues), C-heptad repeat (CHR), and KE (Kennedy epitope) (FIG. 3A). Binding to V3 dominated the linear specificities for all groups but was highest for the MVA-gp120 group (FIG. 3A).

When the magnitude of binding to each linear epitope was compared, significant differences (P<0.05, Exact Wilcoxon Rank Sum test) were observed among groups for binding to epitopes in C2, C4, and C5 following either the 2$^{nd}$ (wk28) or 3$^{rd}$ (wk 42) boost. Highly significant differences (raw p<0.01) were found for C2.2 (MVA+MVA-gp140 and MVA+gp120>MVA-only) at wk42 and C5.1 (MVA+MVA-gp140>MVA-only and MVA+gp120) and C5.2 (MVA+MVA-gp140>MVA-only) at wk28. Due to the large number of samples that were saturated for binding to V3.1, differences among groups for V3.1 binding could not be accurately evaluated.

The contribution of each epitope to the total Env linear epitope binding was evaluated by determining the percentage of the binding intensity for each epitope within the total Env linear epitope binding intensity. Among the 3 groups, the MVA+gp120 group was the most focused on V3, with 81.1% and 70.8% of total linear epitope binding (group median) targeting V3 at wk28 and wk42 respectively, compared to 34.2% to 49.9% for other groups (FIG. 3A and data not shown). The MVA-only group showed a trend for higher proportions of binding responses targeting KE, with 23.2% and 17.1% of total linear epitope binding intensities targeting KE at wk28 and wk42 respectively, compared to 0.8% to 6.1% for other groups (FIG. 3A and data not shown). The MVA+MVA-gp140 group showed a trend for higher proportions of binding responses targeting V5 and C2 (epitope C2.2) compared to the other groups (FIG. 3A). Overall, the MVA only, MVA+gp120, and MVA+MVA-gp140 groups had 3, 1, and 4 epitopes respectively that contributed to >5% binding at both time points (FIG. 3A and data not shown).

Figure 3B:
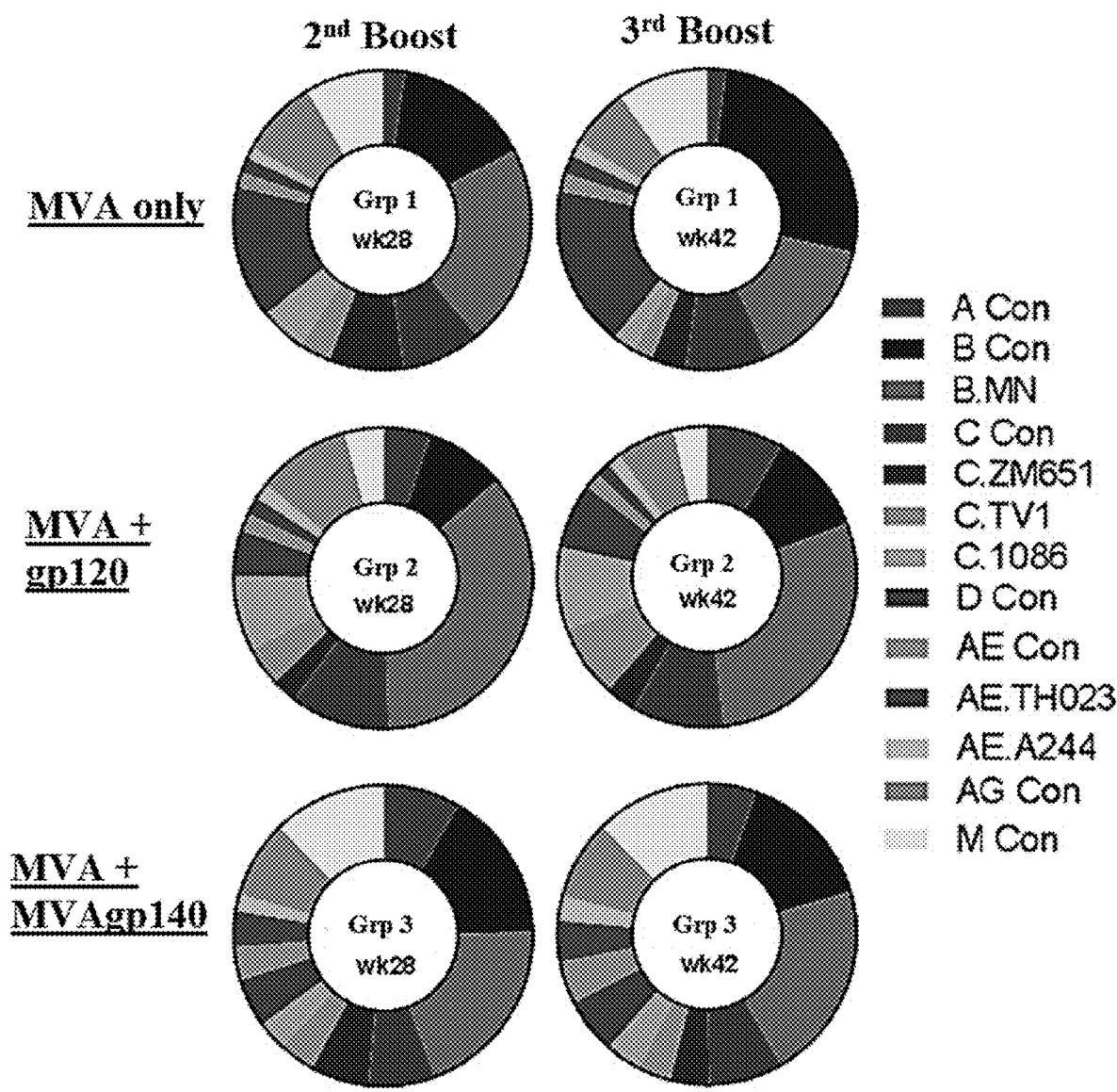

Cross-clade breadth of Env linear epitope binding was evaluated by the relative intensities to peptides of different clades/strains in the peptide microarray (FIG. 3B). Binding responses to different clades were generally similar among vaccine groups and at the two tested timepoints (following the 2$^{nd}$ and 3$^{rd}$ boosts). All groups bound most strongly to clade B sequences. The MVA+gp120 group had slightly higher proportions of binding to clade C sequences than the other 2 groups, with binding to clade C sequences (including consensus C, C.ZM651, C.TV1, and C.1086) accounting for 25.8% and 29.9% of total linear binding at wk28 and wk42 respectively, compared to 17.2% to 25.3% for other groups. The MVA+MVA-gp140 groups showed the most "balanced" coverage of different clades, with proportions of 12 strains (out of 13 total) higher than 3% for both time points compared to 7 strains and 9 strains for MVA only and MVA_gp120 groups respectively (FIG. 3B and data not shown). Proportions of binding for clade AE strains (including consensus AE, AE.A244, and AE.TH023) were 9.1% and 11.6% for the MVA+MVA-gp140 group at wk28 and wk42, compared to 4.4% to 5.5% for the other groups.

Avidity of antibody responses. The avidity of the antibody elicited for three linear epitopes: clade B V3, clade C V3, and gp41 ID was measured in a BAMA-based avidity index assay (Wei, X., et a, 2010, *J Virol* 89:4690-4695). For all animals/epitopes where the avidity indices were quantifiable, avidity indices were higher after the 3$^{rd}$ than the 2$^{nd}$ boost.

Figures 4A, 4B, 4C:
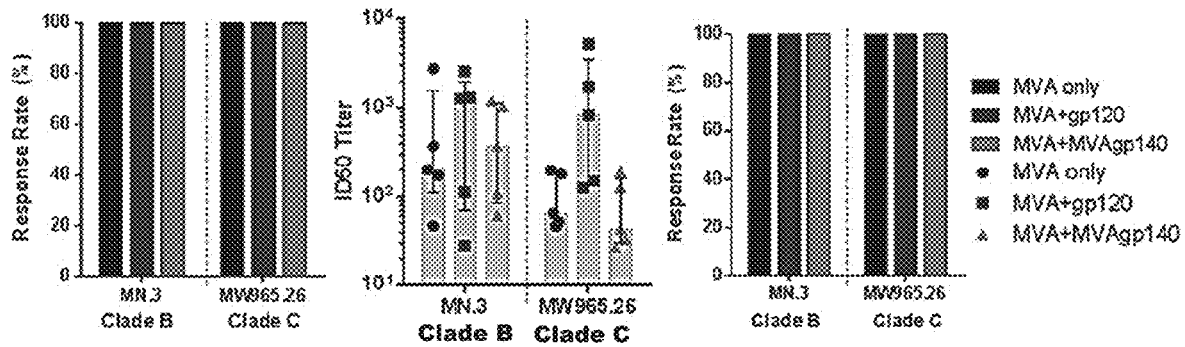
FIG. 4A to FIG. 4H provides data for GV-M1 showing Positivity rates and ID50 titers of serum neutralization against Tier 1A (FIG. 4A-FIG. 4D) and Tier 1B and Tier 2 (FIG. 4E-FIG. 4H) viruses measured in TZM-bl cells. Shaded columns represent group medians and error bars represent interquartile ranges in panels FIG. 4B, FIG. 4D, FIG. 4F, and FIG. 4H. * indicates p<0.05 and ** p<0.01 for pair wise comparison (exact Wilcoxon rank sum test).
Figures 4D, 4E, 4G:
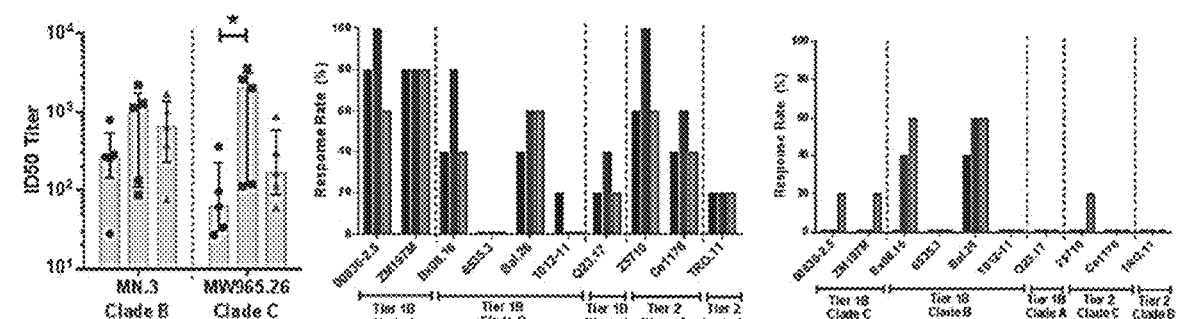

Neutralizing antibody responses. Sera from the 3 groups neutralized Tier 1A, Tier 1B and some Tier 2 viruses. Animals from all vaccine groups developed neutralizing antibodies against Tier 1 MN.3 (clade B) and MW965.26 (clade C) viruses with $ID_{50}$ titers up to 5274 (FIG. 4A-4D). The MVA+gp120 group showed the highest titers post both the $2^{nd}$ and $3^{rd}$ boosts, and the difference was significant between MVA+gp120 and MVA-only groups post the $3^{rd}$ boost for MW965.26 (raw-p=0.03, exact Wilcoxon rank sum test; FIG. 4D).

Figure 4F:
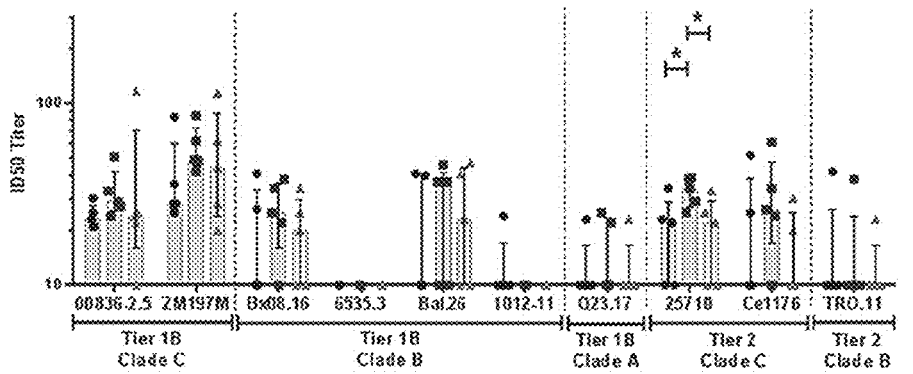
Figure 4H:
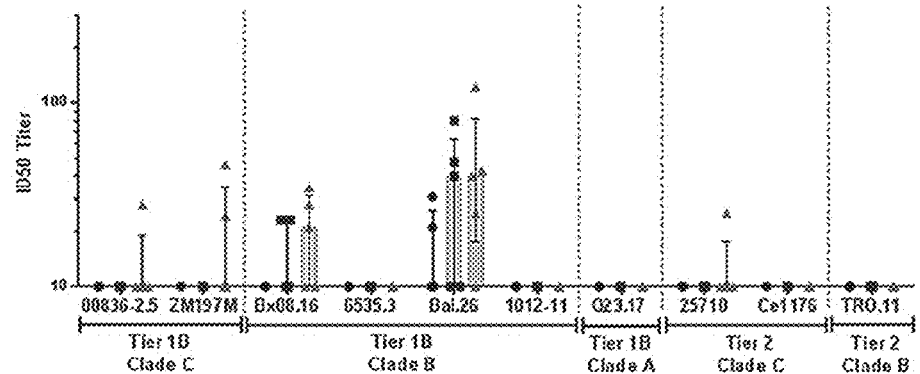
Figure 5A:
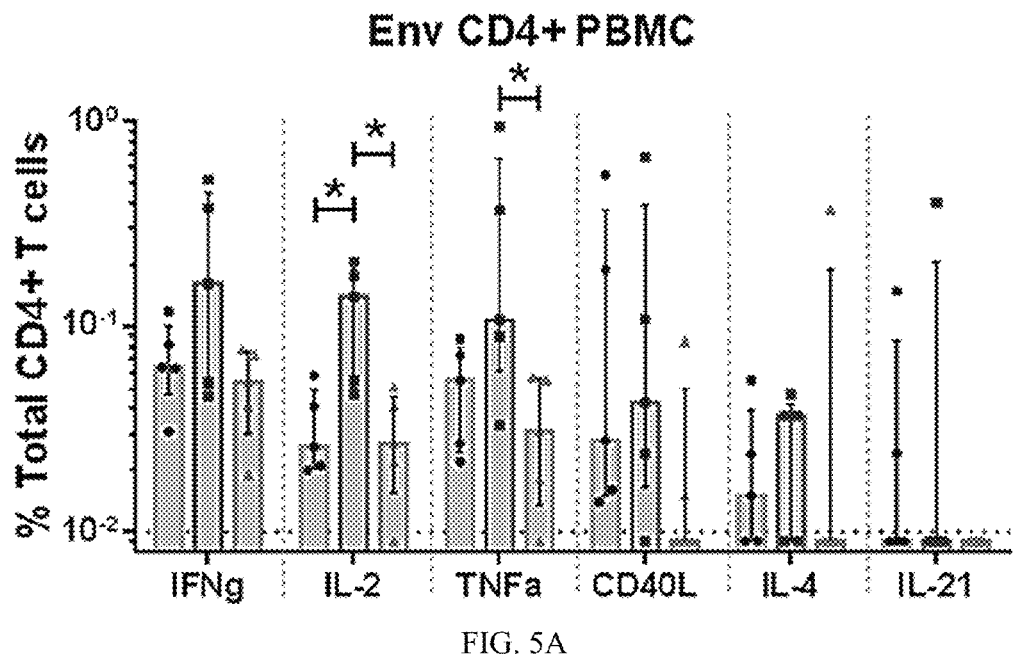
FIG. 5A and FIG. 5B Provides Env-specific T-cell responses for GV-M1. ICS was used to score responding T cells. Env-specific CD4+(FIG. 5A) and CD8+ T cells (FIG. 5B) in PBMCs. Tests were done at one week following the $3^{rd}$ boost. * indicates p<0.05 for pair wise comparison (exact Wilcoxon rank sum test).
Figure 5B:
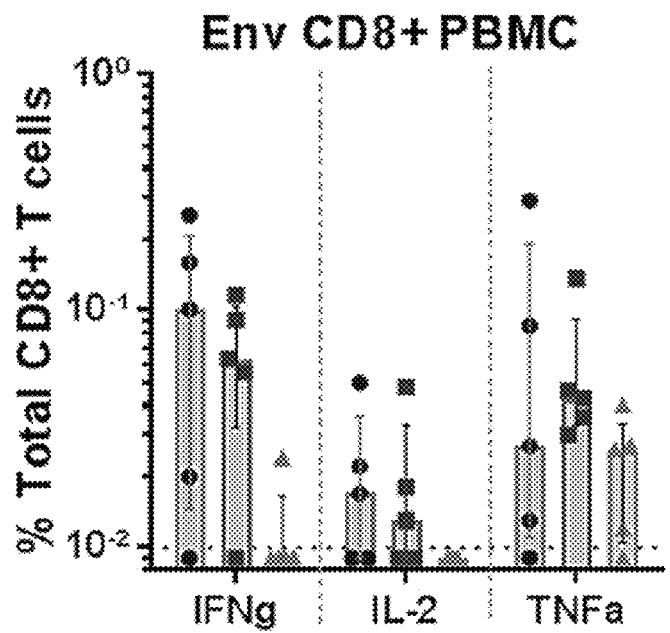

A subset of vaccinated animals developed neutralizing antibodies against Tier 1B viruses with titers up to 122 at wk28 (FIGS. 4E and 4F). The MVA+gp120 group trended higher for magnitudes of neutralizing Ab against both clade C and non-clade C Tier 1B viruses than the other 2 groups. Except for Bal, the response rates and titers were lower for the Tier1B viruses after the $3^{rd}$ than the $2^{nd}$ MVA boost, (FIG. 3E-H). This contrasted with the neutralizing activity for the Tier 1A viruses, which remained at similar positivity rates and titers at wk28 and wk42 for all 3 groups. This decline in activity was particularly evident for the 2 tested Clade C Tier 1B viruses. After the $2^{nd}$ MVA boost, response rates to both clade C Tier 1B viruses were 60% or greater and several titers were above 1:80. After the $3^{rd}$ MVA boost, the highest response rate was 20% and titers were below, or close to background (1:20). The MVA+MVA-gp140 group maintained low level of responses slightly better than the other 2 groups (FIGS. 4G&5H). Neutralization for clade B Tier 1B virus BX08.16 and clade A Tier 1B virus Q23.17 also declined for both positivity rates and serum titers, especially for the MVA-only and MVA+gp120 groups, (FIGS. 4E and 4H).

Notably, vaccinated animals developed low levels of neutralizing antibodies ($ID_{50}$ titers up to 61) against Tier 2 viruses after the $2^{nd}$ boost, with positivity rates ranging from 40% to 100% for 2 clade C Tier 2 viruses (25710-2.43 and Ce1176_A3) and being 20% for the clade B Tier 2 virus TRO.11 (FIGS. 4E and 4F). The MVA+gp120 group showed the highest positivity rate and titer among the 3 groups, with titers significantly higher than for the other 2 groups for isolate 25710-2.43 (raw-p<0.05, Exact Wilcoxon Rank Sum). Neutralization against Tier 2 viruses was undetectable following the $3^{rd}$ boost for all but one animal in the MVA-gp140 supplemented group (FIGS. 4E and 4H).

ADCC responses. In assays using B63521Δ11 gp120-coated target cells, ADCC activity was detected in 100% of animals in both supplemented groups. Consistent with its high titers of elicited Ab for B63521Δ11, the MVA+gp120 group showed higher ADCC titers and peak granzyme B activity than the other 2 groups (raw-p<0.05 at wk28 and P<0.01 at wk42, exact Wilcoxon rank sum test). Group median titers were 1:85,000 and 1:800 for the MVA+gp120 and MVA+MVA-gp140 groups respectively post the $2^{nd}$ boost, and 1:40,000 and 1:3,000 respectively after the $3^{rd}$ boost. Assays for ADCC revealed essentially no activity for budding virus (Bal) for any of the immunization conditions (data not shown).

Discussion

The current study compared the magnitude, durability, specificity, breadth, and functional activity of antibody elicited by MVA+gp120 protein boosts, MVA+MVA-gp140 boosts or MVA-only boosts of a DNA-primed response. These results reveal the supplemented boosts eliciting higher, broader and more functional antibody responses than the non-supplemented boosts.

They also reveal the protein-supplemented, but not the MVA supplemented boosts enhancing CD4+ T cell responses.

The goal for supplementing the MVA boosts was to enhance antibody responses to gp120 and the V1V2 region of gp120 over those elicited by the non-supplemented GOVX-B11 DNA/MVA vaccine. Following the $3^{rd}$ and last boost, both the gp120-supplemented and the MVA-gp140-supplemented boosts achieved very similar enhancements of Ab responses to gp120 and the V1V2 region of gp120. Antibody responses to gp120 were 4.3 and 3.0-fold higher to gp120 and 2.1 and 2.5-fold higher for V1V2 for the B63521Δ11mutC gp120 and MVA-gp140 supplemented groups respectively (Table 5). The largest difference in magnitude for supplemented responses were for the vaccine strain-matched B63521Δ11mutC protein, which was enhanced 17.9-fold by the gp120 protein supplement, but only 3.5-fold by the MVA-gp140 supplement. The $2^{nd}$ largest difference was the 8.4-fold enhancement for linear V3 binding for the MVA+gp120 group compared to a 2.6-fold enhancement for the MVA+MVA-gp140 group.

In addition to the magnitude of binding antibody responses, gp120 protein and MVA-gp140 supplements affected the durability of antibody responses and the performance of repeated boosts. The MVA+gp140-supplemented group showed a trend for a slower decline and a more effective $3^{rd}$ boost of responses compared to the MVA+gp120 group. This lower contraction and higher boost with MVA-gp140 suggest that MVA-gp140 may elicit more durable and replenish able responses compared to the gp120 protein boost. While not to be bound by a particular theory, lower levels of pre-boost Ab likely contributed to the efficiency of the $3^{rd}$ MVA-gp140 boost.

In contrast to antibody responses, which were enhanced by both the MVA+gp120 and MVA+gp140 boosts, CD4+ T cells were increased over those elicited by the non-supplemented vaccine by only the gp120 protein supplement. At one week following the $3^{rd}$ boost, the gp120-supplemented boosts enhanced CD4+ responses by 2.5-fold for IFNγ, 5.3-fold for IL-2 and 1.9-fold for TNFα relative to responses in the non-supplemented MVA boosts. At the same time, MVA-gp140 supplemented responses had levels of CD4+ T cells indistinguishable from those of the non-supplemented responses (medians of 0.03 to 0.06% of total CD4+ T cells). The elicitation of higher CD4+ T cells by the gp120-supplemented response is a concern for HIV vaccine development, because responding CD4+ T cells have been hypothesized to potentially enhance infections. (Fouts T R, et al., 2015. Proc Natl Acad Sci USA doi:10.1073/pnas.142366911; Fauci A S, et al., 2014, Science 344:49-51 Lewis G K, et al., 2014, Proc Natl Acad Sci USA 111:15614-156210. Successful prevention of acquisition requires a balance in antibody and CD4+ T cell responses in which virus-specific CD4+ T cells, which are preferential targets for infection (Douek D C, et al., 2002, Nature 417:95-9), do not mute the effect of protective antibodies. Indeed in 4 preclinical trials in which gp120 or gp140 protein boosts have been used with DNA/MVA prototypes of the GOVX-B11 vaccine, the protein boosts have reduced the prevention of acquisition by repeated low dose intrarectal or intravaginal challenges (Amara in preparation) or reduced the control of post infection viremia (Iyer S S, et al., 2015, J Immunol 195:994-1005; Buge S L, et al., 2003, AIDS Res Hum Retroviruses 19:891-900). In 3 of these trials, infection and/or poor control of viremia has directly correlated with the induction of vaccine-specific CD4+ T cells (Iyer S S, et al., 2015, J Immunol 195:994-10050) (Amara, personal communication). Thus, the ability of supplemental MVA-gp140 boosts to increase antibodies without boosting CD4+ T cell responses is favorable for achieving protection by DNA/MVA vaccines.

The supplemental gp120 and MVA-gp140 boosts enhanced functional as well as binding antibody responses. The gp120 supplement enhanced both neutralizing and ADCC responses whereas the MVA-gp140 enhanced ADCC responses. Elicitation of higher neutralizing titers for Tier1A viruses by the protein boost likely reflected the strong ability of the gp120 protein to boost V3 responses. Interestingly, for all three groups, the 2$^{nd}$ MVA boost elicited higher responses to Tier 1B and Tier 2 viruses than the 3$^{rd}$ boost. This phenomenon may reflect multiple protein boosts driving responses away from "neutralizing" conformational epitopes and towards "non-neutralizing" linear epitopes. Both supplemental boosts enhanced ADCC responses for bound B63521Δ11mutC protein. This likely reflects both boosts enhancing binding antibodies to B63521Δ11mutC. The higher ADCC responses elicited by MVA+gp120 than MVA+MVA-gp140 likely reflect the very high titers of binding activity for B63521Δ11mutC elicited by the matched gp120 boost.

In conclusion, the supplementation of MVA boosts in a DNA/MVA vaccine regimen with gp120 protein or MVA-expressed gp140 differed in their ability to enhance CD4+ T cell responses but were similar in their ability to increase levels of Ab for gp120 and the V1V2 region of gp120. Specifically, the MVA+gp120 boost increased the median magnitude of responding CD4+ T cells, while the MVA-gp140 supplement did not detectably increase CD4+ T cell responses over those elicited by the non-supplemented vaccine. Elicited antibody responses peaked earlier and contracted more strongly for the protein than the MVA-gp140 boosts. Following the 3$^{rd}$ boost, both supplements had increased median magnitudes/breadths of peak binding Ab for the ARP gp120 panel by 3 to 4.3-fold and for the ARP V1V2 panel by 2.1 to 2.5-fold. These data suggest that for DNA/MVA vaccines, MVA-gp140 supplemented boosts are superior to gp120 protein supplemented boosts for eliciting protective non-neutralizing antibodies because of their ability to boost antibodies without increasing CD4+ T cell targets for infection.

Example 2: GV-M3—Boosting an Immune Response to HIV Using a Bivalent B.63521Δ1111mutC+FLSC Peptide Boost or a MVA Expressing Secreted gp140 Boost for the GOVX-B11 DNA/MVA Vaccine An ongoing GV-M3 trial is a pivotal preclinical protection study for the value of a bivalent protein boost for GOVX-B11. Previous work cited in Example 1, evaluated a gp120 protein (B.63521Δ11mutC) and a MVA-expressing secreted gp140 (MVA expressed ADA gp140) as boosts for the GOVX-B11 HIV vaccine and found both met the criteria for advancement to a preclinical non-human primate protection study. This project improves the B.6352111mutC boost by adding a 2nd CD4-induced gp120 protein (full length single chain, FLSC) to complement the immunogenicity of B.63521Δ11mutC, a receptor binding form of Gp120.

This animal study includes a repeated low-dose intra-rectal challenge with a pathogenic clade B SHIV (to be selected at the time of challenge). The repeated low-dose challenge represents a widely used preclinical model for infection of men who have sex with men and will provide valuable data on the protective potential of GOVX-11 with or without a gp120 protein or MVA-expressed gp140 boost. The immunogenicity as well as protection results will play a critical role in determining the form of GOVX-B11 (protein boosted, MVA-gp140 boosted, or both), that progress to further clinical testing.

GV-M3 differs from GV-M1 (Example 1) in having 7-8 animals per group, a bivalent protein boost (B63521Δ11 plus FLSC), and in being a challenge study. The Division of AIDS, NIAID, NIH, is conducting a parallel macaque study, P192, that will bring the total animals per group to 15. GV-M3 is also different from GV-M1 in using 300 μg of each protein for a total of 600 μg of gp120 as opposed to the 100 μg used in GV-M1

TABLE 6

Trial Groups, Vaccination schedule in weeks for GV-M3

| | | Vaccination schedule in weeks for GV-M3[1] | | | | | 10 weekly rectal challenges Wk 64-73 |
|---|---|---|---|---|---|---|---|
| Group | N | T1 Wk 0 | T2 Wk 8 | T3 Wk16 | T4 Wk 24 | T5 Wk 40 | |
| 1 | 8 | D | D | M | M | M | SHIV |
| 2 | 7 | D | D | M + Pr | M + Pr | M + Pr | SHIV |
| 3 | 7 | D | D | M + M140 | M + M140 | M + M140 | SHIV |
| 4 | 8 | S | S | S | S | S | SHIV |

[1]D, pGA2/JS7 DNA; M, MVA/HIV62B, Pr, B63521Δ11 plus FLSC in alum; M140, MVA/HIVgp140; S, saline; SHIV, pathogenic clade B SHIV The reason for adding a 2$^{nd}$ protein to the gp120 protein boost was that in the GV-M1 trial, the B.63521Δ11 boost did not increase antibody responses to the V1V2 region of gp120 as strongly as desired. B.63521 is a transmitted/founder Env selected for favorable ability to present epitopes present in the receptor binding form of Env{Liao, 2013 #7304}. The 2$^{nd}$ protein added to the boost was selected for its ability to present the post binding CD4-induced form of Env. This protein termed full length single chain (FLSC) was specifically developed as a fusion of gp120 and the D1 and D2 receptor binding domains of CD4 to present a CD4-induced form of Env{Fouts, 2000 #8282}. Thus while B63521Δ11 was chosen to boost receptor binding epitopes on Env, FLSC was chosen to boost specificities on the CD4-induced form of Env, including V1V2. Thus, the two protein boosts complement each other in the specificities of the antibodies that they should enhance. Also, in GV-M3, higher levels of gp120 protein were used in the boost, (300 μg of each for a total of 600 μg).

Figure 6A:
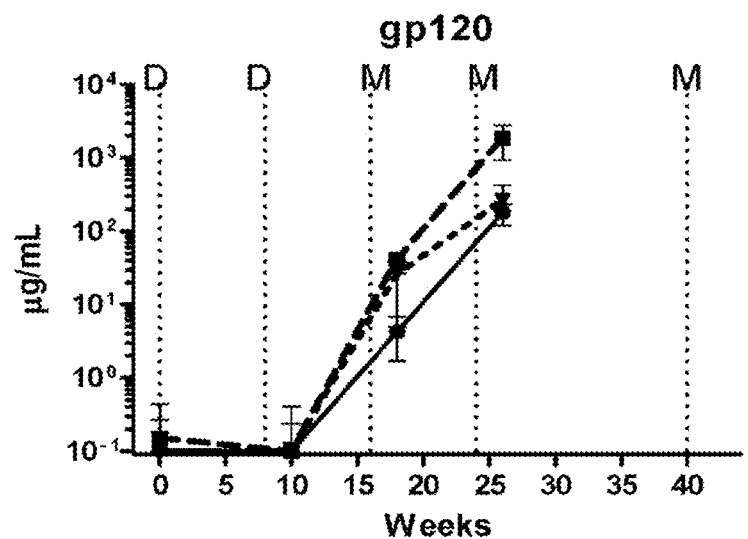
FIG. 6A and FIG. 6B. Provides temporal antibody responses for gp120 (FIG. 6A) and V1V2 (FIG. 6B) in GV-M3. Enzyme-linked immunosorbent assays were conducted to estimate levels of elicited antibody against a standard curve of monkey IgG. Con6gp120 is a consensus gp120 produced at the Duke Human Vaccine Institute. V1V2 is a conformational V1V2: gp70_B.caseAV1V2 produced at the Duke Human Vaccine Institute.
Figure 6B:
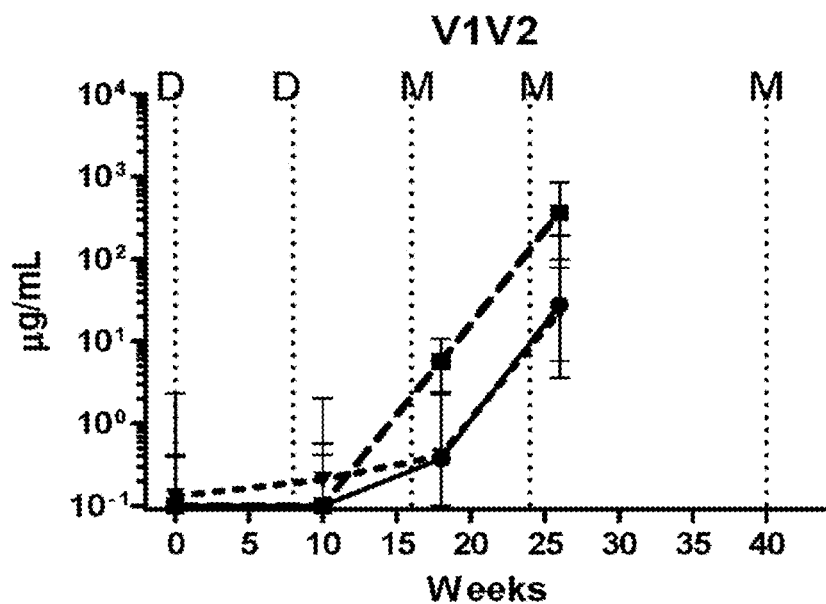

The results at T4 (the 2$^{nd}$ boost in the GV-M3 trial) for temporal antibody responses are provided in FIG. 6. The results show the bivalent protein boost enhancing V1V2 responses by 10-fold over those in the MVA-only boosts as opposed to the 2 fold in GV-M1 that used a monovalent B63521Δ11mutC protein boost and 6-times lower levels of protein. Estimated levels of antibodies to gp120 were also boosted higher by the gp120 protein in GV-M3 than in GV-M1: 6.3 fold over MVA-only as opposed to 4.3 fold in GV-M1. After the 2$^{nd}$ boost, estimated median levels of antibodies for a consensus gp120 are 1150 μg per ml of serum and those for V1V2, 370 μg per ml of serum. Post the 2$^{nd}$ MVA boost, the titers of Ab-elicited by the MVA-gp140 supplement were only marginally higher than those elicited by MVA-only. However, the better durability of Ab elicited by MVA-gp140 and the better ability of MVA-gp140 to provide late boosts (FIG. 3) may result in the levels of Ab elicited by these two boosts being more similar after the 3$^{rd}$ boost.

Figure 7A:
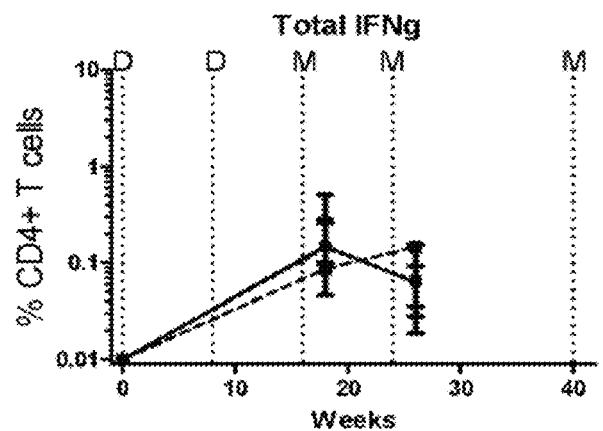
FIG. 7A to FIG. 7C. Provides temporal CD4+ T cell responses for Env in GV-M3. Intracellular cytokine analyses were used to determine cytokine producing cells post stimulation with a pool of ADA Env peptides (15-mers overlapping by 11). Showing Total IG Ng (FIG. 7A), Total IL-2 (FIG. 7B) and Total Ng+ and IL-2+(FIG. 7C) responses.
Figure 7B:
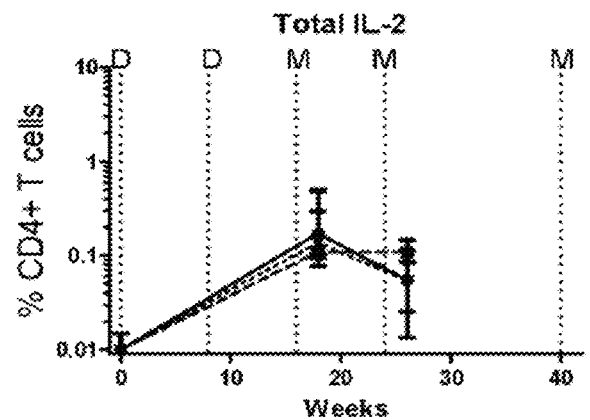
Figure 7C:
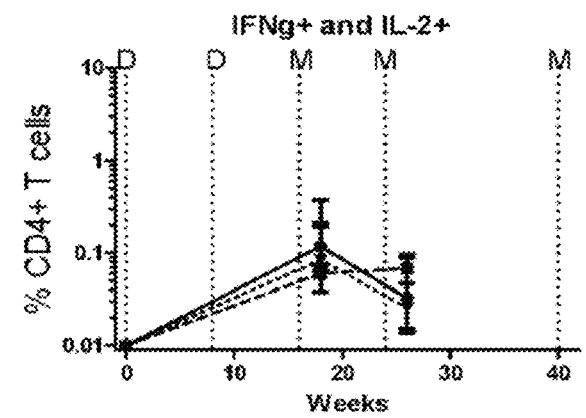

Analyses of T cell responses revealed that, similar to the results in GV-M1, the protein boosts trend to elicit higher CD4+ T cell responses to Env than the MVA-only or MVA+MVA-gp140 boosts (FIG. 7). Whereas the magnitudes of CD4+ T cell responses are declining following the $2^{nd}$ MVA or MVA plus MVA-gp140 boosts, these responses are holding or increasing for the MVA plus gp120 boosted group. Thus, although we await the results of the $3^{rd}$ boost for final results for GV-M3, the results after the $2^{nd}$ MVA boost are replicating the GV-M1 result that protein boosts enhance CD4+ T cell responses over those elicited by MVA boosts or MVA boosts supplemented with MVA-gp140.

The invention claimed is:

1. A method for inducing an immune response to a human immunodeficiency virus (HIV) comprising administering to a human in need thereof:
   i) a prime vaccination comprising an effective amount of a vector encoding HIV antigens that, when expressed, are displayed on virus-like particles; and
   ii) a boost vaccination comprising
      a) an effective amount of a modified vaccinia Ankara (MVA) vector encoding a membrane-bound HIV envelope (Env) protein that, when expressed, is displayed on virus-like particles,
      b) an effective amount of a first HIV Env protein comprising a mutated form of gp120, and,
      c) an effective amount of a second HIV Env protein comprising a CD4-induced form of gp120.

2. The method of claim 1, wherein the MVA vector is MVA/HIV62B.

3. The method of claim 1, wherein the mutated form of gp120 comprises a B.63521Δ11mutC receptor-binding subunit of gp120.

4. The method of claim 1, wherein the CD4-induced form of gp120 comprises the full length single chain (FLSC) CD4-induced form of gp120.

5. The method of claim 1, wherein the first HIV Env protein
   is a B.63521Δ11mutC receptor-binding subunit of gp120 and the second HIV Env protein is FLSC CD4-induced form of gp120.

6. The method of claim 1, wherein the first HIV Env protein and second HIV Env protein are each administered at a concentration of between about 100 to 300 µg.

7. The method of claim 1, wherein the first HIV Env protein and second HIV Env protein are each administered at a concentration of about 300 ug.

8. The method of claim 1, wherein the first HIV Env protein is administered in a composition comprising an adjuvant and the second HIV Env protein is administered in a composition comprising an adjuvant.

9. The method of claim 8, wherein the adjuvant comprises an alum adjuvant.

10. The method of claim 8, wherein the adjuvant comprises an aluminum phosphate.

11. The method of claim 8, wherein the adjuvant comprises an aluminum hydroxide.

12. A method for boosting an immune response to a human immunodeficiency virus (HIV) comprising administering to a human in need thereof a boost vaccination comprising:
   a) an effective amount of an MVA vector encoding a membrane-bound HIV Env protein that, when expressed, is displayed on virus-like particles,
   b) an effective amount of a first HIV Env protein comprising a mutated form of gp120, and
   c) an effective amount of a second HIV Env protein comprising a CD4-induced form of gp120,
   wherein, prior to the administration of the boost vaccination, the human has previously been administered one or more vaccinations comprising an HIV antigen.

13. The method of claim 12, wherein the MVA vector is MVA/HIV62B.

14. The method of claim 12, wherein the mutated form of gp120 comprises a B.63521Δ11mutC receptor-binding subunit of gp120.

15. The method of claim 12, wherein the CD4-induced form of gp120 comprises the full-length single chain (FLSC) CD4-induced form of gp120.

16. The method of claim 12, wherein the first HIV Env protein comprises B.63521Δ11mutC receptor-binding subunit of gp120 and the second HIV Env protein is FLSC CD4-induced form of gp120.

17. The method of claim 12, wherein the first HIV Env protein and second HIV Env protein are each administered at a concentration of between about 100 to 300 µg.

18. The method of claim 12, wherein the first HIV Env protein and second HIV Env protein are each administered at a concentration of about 300 ug.

19. The method of claim 12, wherein the first HIV Env protein is administered in a composition comprising an adjuvant and the second HIV Env protein is administered in a composition comprising an adjuvant.

20. The method of claim 19, wherein the adjuvant comprises an alum adjuvant.

21. The method of claim 19, wherein the adjuvant comprises an aluminum phosphate.

22. The method of claim 19, wherein the adjuvant comprises an aluminum hydroxide.

* * * * *

UNITED STATES PATENT AND TRADEMARK OFFICE
CERTIFICATE OF CORRECTION

| | |
|---|---|
| PATENT NO. | : 11,098,086 B2 |
| APPLICATION NO. | : 16/077215 |
| DATED | : August 24, 2021 |
| INVENTOR(S) | : Harriet Robinson |

It is certified that error appears in the above-identified patent and that said Letters Patent is hereby corrected as shown below:

In the Specification

Please insert the following paragraph at Column 1, after the "CROSS REFERENCE TO RELATED APPLICATIONS" section and before the "FIELD OF THE INVENTION" section:
--STATEMENT OF FEDERALLY FUNDED RESEARCH
This invention was made with government support under grant R44AI106422 awarded by the National Institutes of Health. The government has certain rights in the invention.--

Signed and Sealed this
Seventh Day of November, 2023

Katherine Kelly Vidal
*Director of the United States Patent and Trademark Office*